United States Patent [19]

McKittrick et al.

[11] Patent Number: 5,476,847
[45] Date of Patent: Dec. 19, 1995

[54] DERIVATIVES OF PHOSPHINIC ACID USEFUL AS ENDOTHELIN CONVERTING ENZYME INHIBITORS

[75] Inventors: Brian A. McKittrick, Bloomfield; Michael F. Czarniecki, Watchung; Samuel Chackalamannil, East Brunswick, all of N.J.; Shin Chung, Kyongki-Do, Rep. of Korea; Shawn DeFrees, San Marcos, Calif.; Andrew W. Stamford, Chatham Twp., N.J.

[73] Assignee: Schering Corporation, Kenilworth, N.J.

[21] Appl. No.: 267,630

[22] Filed: Jun. 29, 1994

[51] Int. Cl.$^6$ .................... A61K 31/405; A61K 31/66; C07D 209/14; C07F 9/36
[52] U.S. Cl. .................... 514/80; 514/90; 514/112; 514/119; 514/94; 544/139; 544/143; 548/119; 548/414; 558/170; 562/15
[58] Field of Search .................... 548/414, 119; 514/80, 90, 94, 112, 119; 558/170; 562/15

[56] References Cited

U.S. PATENT DOCUMENTS

| | | | |
|---|---|---|---|
| 4,452,791 | 6/1984 | Ryono et al. | 424/200 |
| 4,661,473 | 4/1987 | Boger et al. | 514/16 |
| 4,716,155 | 12/1987 | Karanewsky et al. | 514/89 |
| 5,006,651 | 4/1991 | Broadhurst et al. | 540/463 |
| 5,338,726 | 8/1994 | Shiosaki et al. | 514/17 |

FOREIGN PATENT DOCUMENTS

| | | |
|---|---|---|
| 209848 | 1/1987 | European Pat. Off. . |
| 209897 | 1/1987 | European Pat. Off. . |
| 337714 | 10/1989 | European Pat. Off. . |
| WO91/151 | 10/1991 | WIPO . |

OTHER PUBLICATIONS

Inman, J. K., Chapter 6 in Gross, E. et al. *The Peptides. Analysis, Synthesis, Biology*, vol. 3 (Acadamic Press, New York), pp. 268–272 (1981).
Grant, R. et al. *Grant & Hackh's Chemical Dictionary* (McGraw–Hill, New York), pp. 31 and 299 (1986).
S. Bertenshaw, et al, *J. Med. Chem.*, 36 (1993), pp. 173–176.
A. Benigni, et al, *Kidney International*, 44 (1993), pp. 440–444.
S. Vermulapalli, et al, *Life Sciences*, 53 (1993), pp. 783–793.
S. Vermulapalli, et al., *J. Pharmacol. Exp. Therap.*, 262 (1992), pp. 1062–1069.
W. Schaffner, et al, *Anal. Biochem.*, 56 (1973), pp. 502–514.
E. Baylis, et al, *J. Chem. Soc. Perkin Trans. I* (1984), pp. 2845–2853.

*Primary Examiner*—Mukund J. Shah
*Assistant Examiner*—King Lit Wong
*Attorney, Agent, or Firm*—Anita W. Magatti; Eric S. Dicker

[57] ABSTRACT

Phosphinic acid derivatives of the structural formula $$R_6 \underset{H}{\overset{R_1 \; R_2}{\underset{|}{N}}}\underset{OR}{\overset{O}{\underset{\|}{P}}}(\,)_n \underset{O}{\overset{R_3 \; R_4}{\underset{\|}{\phantom{C}}}} A_1 - R_5$$

or a pharmaceutically acceptable salt thereof, wherein
R is H, alkyl or alkanoyloxymethylene;
$R_1$, $R_2$, $R_3$ and $R_4$ are H, alkyl, alkenyl, alkenylalkyl, aryl, arylalkyl, heteroaryl, heteroarylalkyl, hydroxyalkyl, carboxyalkyl, thioalkyl, alkoxythioalkyl, aminoalkyl, alkylaminoalkyl, cycloalkyl-substituted alkyl or heterocycloalkyl; or $R_1$ and $R_2$ form a cycloalkyl ring of 3–8 members and $R_3$ and $R_4$ are as defined; or $R_3$ and $R_4$ form a cycloalkyl ring of 3–7 members and $R_1$ and $R_2$ are as defined; or $R_1$ and $R_2$ together, and $R_3$ and $R_4$ together, each form a cycloalkyl ring;
$R_5$ is —$OR_9$ or —$NHR_9$, wherein $R_9$ is hydrogen or alkyl;
n is 0 or 1;
$A_1$ is p-aminobenzoyl or p-aminobenzenesulfonyl, or $A_1$ and $R_5$ together form a radical of an α-aminoacyl derivative; and
$R_6$ is phenylmethoxycarbonyl, arylcarbonyl, heteroarylcarbonyl or —$A_2$—$R_7$, wherein $A_2$ is a divalent α-aminoacyl radical, and $R_7$ is a substituent on the α-amino atom selected from H, $R_8OCO$—, $R_8SO_2$— and $R_8NHCO$—, wherein $R_8$ is aryl, arylmethyl or ($C_1$–$C_8$)alkyl;
are disclosed for use as endothelin converting enzyme inhibitors; also disclosed are a genus of novel compounds wherein $R^3$ and $R^4$ form a cycloalkyl ring, and pharmaceutical compositions comprising said novel compounds.

29 Claims, 6 Drawing Sheets

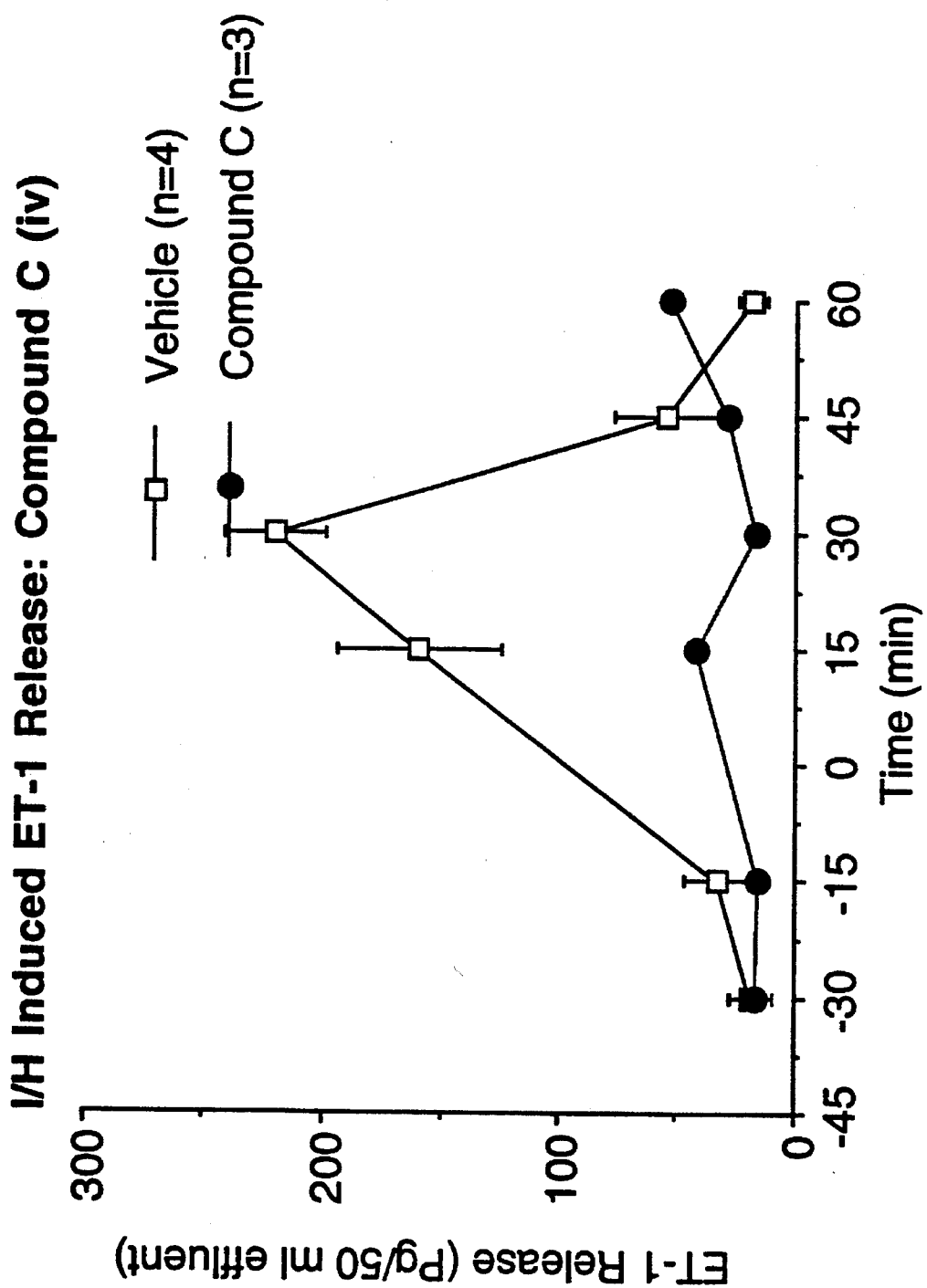

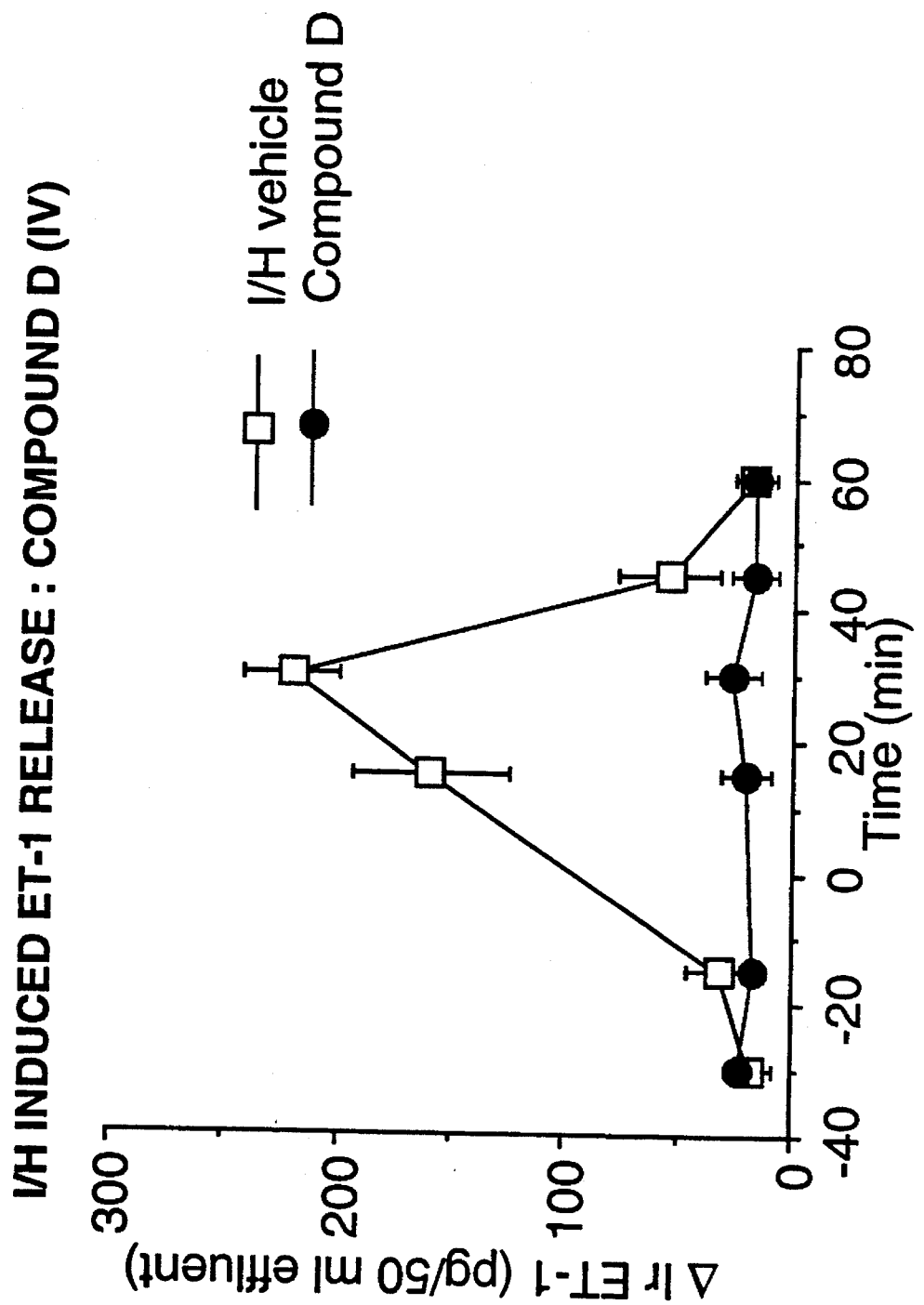

DERIVATIVES OF PHOSPHINIC ACID USEFUL AS ENDOTHELIN CONVERTING ENZYME INHIBITORS

BACKGROUND

This invention relates to the use of phosphinic acid derivatives as inhibitors of endothelin converting enzyme, to novel phosphinic acid derivatives and to pharmaceutical compositions comprising said novel compounds.

Endothelins are a family of peptides, including endothelin-1, endothelin-2 and endothelin-3 (ET-1, ET-2 and ET-3), which show potent vasoconstrictive and mitogenic activity. ET-1, approximately 100 times more potent than its precursor, big-endothelin-1 (BET-1), is believed to be liberated from BET-1 by an endothelin converting enzyme (ECE). See S. Bertenshaw, et al, *J. Med. Chem.*, 36(1993), p. 173–176. Endothelin receptor blockers have been reported to protect against injury in renal disease progression. See A. Benigni, et al, *Kidney International*, 44 (1993), p. 440–444. Inhibition of ECE, which will also make endothelin unavailable to its receptors, can therefore treat disease states characterized by excessive production of endothelin. Therefore, phosphinic acid derivatives of this invention are useful for the treatment of myocardial ischemia, congestive head failure, arrhythmia, hypertension, pulmonary hypertension, asthma, cerebral vasospasm, subarachanoid hemorrhage, pre-eclampsia, wound healing, control of menstruation, acute/chronic renal failure, renal ischemia, renal glomerulosclerosis, atherosclerosis, Buergers disease, Takayasu's arteritis, complications in diabetes, pulmonary carcinoma, gastrointestinal disorders, endotoxic shock, and septicemia.

SUMMARY OF THE INVENTION

Compounds for use as endothelin converting enzyme inhibitors are represented by the formula I

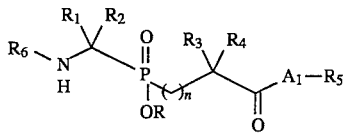

or a pharmaceutically acceptable salt thereof, wherein

R is H, $(C_1-C_8)$alkyl or alkanoyloxymethylene;

$R_1$, $R_2$, $R_3$ and $R_4$ are independently selected from the group consisting of H, $(C_1-C_8)$alkyl, $(C_1-C_8)$alkenyl, $(C_1-C_8)$alkenyl$(C_1-C_8)$alkyl, aryl, aryl$(C_1-C_8)$alkyl, heteroaryl, heteroaryl$(C_1-C_8)$alkyl, hydroxy$(C_1-C_8)$alkyl, carboxy$(C_1-C_8)$alkyl, thio$(C_1-C_8)$alkyl, $(C_1-C_6)$alkoxythio$(C_1-C_8)$alkyl, amino$(C_1-C_8)$alkyl, $(C_1-C_8)$alkylamino$(C_1-C_8)$alkyl, cycloalkyl-substituted$(C_1-C_8)$alkyl and heterocycloalkyl; or $R_1$ and $R_2$, together with the carbon to which they are attached, form a cycloalkyl ring of 3 to 8 members and $R_3$ and $R_4$ are as defined above; or $R_3$ and $R_4$, together with the carbon to which they are attached, form a cycloalkyl ring of 3 to 7 members and $R_1$ and $R_2$ are as defined above; or $R_1$ and $R_2$ together, and $R_3$ and $R_4$ together, each form a cycloalkyl ring as defined above;

$R_5$ is $-OR_9$ or $-NHR_9$, wherein $R_9$ is hydrogen or $(C_1-C_8)$alkyl;

n is 0 or 1;

$A_1$ is p-aminobenzoyl or p-aminobenzenesulfonyl, or $A_1$ and $R_5$ together form a radical of an α-aminoacyl derivative, wherein $A_1$ is a divalent α-aminoacyl radical attached to the molecule at the α-amino group, and wherein $R_5$ is attached to the acyl terminus of $A_1$;

$R_6$ is phenylmethoxycarbonyl, arylcarbonyl, heteroarylcarbonyl or $-A_2-R_7$, wherein $A_2$ is a divalent α-aminoacyl radical attached to the molecule at the acyl terminus, and wherein $R_7$ is a substituent on the α-amino atom selected from the group consisting of H, $R_8OCO-$, $R_8SO_2-$ and $R_8NHCO-$, wherein $R_8$ is aryl, arylmethyl or $(C_1-C_8)$alkyl.

Novel compounds of the present invention are those represented by structural formula II:

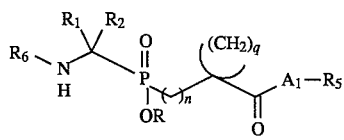

or a pharmaceutically acceptable salt thereof, wherein

R is H, $(C_1-C_8)$alkyl or alkanoyloxymethylene;

$R_1$ and $R_2$, are independently selected from the group consisting of H, $(C_1-C_8)$alkyl, $(C_1-C_8)$alkenyl, $(C_1-C_8)$alkenyl$(C_1-C_8)$alkyl, aryl, aryl$(C_1-C_8)$alkyl, heteroaryl, heteroaryl$(C_1-C_8)$alkyl, hydroxy$(C_1-C_8)$alkyl, carboxy$(C_1-C_8)$alkyl, thio$(C_1-C_8)$alkyl, $(C_1-C_6)$alkoxythio$(C_1-C_8)$alkyl, amino$(C_1-C_8)$alkyl, $(C_1-C_8)$alkylamino$(C_1-C_8)$alkyl, cycloalkyl-substituted$(C_1-C_8)$alkyl and heterocycloalkyl; or $R_1$ and $R_2$, together with the carbon to which they are attached, form a cycloalkyl ring of 3 to 8 members;

$R_5$ is $-OR_9$ or $-NHR_9$, wherein $R_9$ is hydrogen or $(C_1-C_8)$alkyl;

n is 0 or 1;

q is 4 to 6

$A_1$ is p-aminobenzoyl or p-aminobenzenesulfonyl, or $A_1$ and $R_5$ together form a radical of an α-aminoacyl derivative, wherein $A_1$ is a divalent α-aminoacyl radical attached to the molecule at the α-amino group, and wherein $R_5$ is attached to the acyl terminus of $A_1$;

$R_6$ is phenylmethoxycarbonyl, arylcarbonyl, heteroarylcarbonyl or $-A_2-R_7$, wherein $A_2$ is a divalent α-aminoacyl radical attached to the molecule at the acyl terminus, and wherein $R_7$ is a substituent on the α-amino atom selected from the group consisting of H, $R_8OCO-$, $R_8SO_2-$ and $R_8NHCO-$, wherein $R_8$ is aryl, arylmethyl or $(C_1-C_8)$alkyl.

Preferred compounds of formula I are those wherein $A_1$-$R_5$ is L-tryptophanyl, L-tyrosinyl or L-O-methyl tyrosinyl. Also preferred are compounds of formula I wherein $R_1$ and $R_2$ are independently selected from the group consisting of H, arylalkyl, branched alkyl and cycloalkyl. Especially preferred are compounds wherein one of $R_1$ and $R_2$ is hydrogen and the other is benzyl, 2-naphthylmethyl, or branched alkyl.

Another group of preferred compounds is that wherein $R_3$ and $R_4$ are independently selected from the group consisting of hydrogen and alkyl, with preferred alkyl groups being iso-propyl and iso-butyl, or $R_3$ and $R_4$, together with the carbon to which they are attached, form a cycloalkyl ring of 5 or 7 members.

In preferred compounds of formula I, n is 1. Also preferred are compounds of formula I wherein R is hydrogen and $R_5$ is hydroxy.

Still another group of preferred compounds of formula I is that wherein $R_6$ is phenylmethoxycarbonyl or $A_2$—$R_7$, wherein $A_2$ is an α-amino acyl radical derived from a natural α-amino acid in the R or S chiral form, preferably lysine, ε-CBZ lysine, arginine, isoleucine, leucine, valine, phenylalanine, alanine, glycine or tyrosine, and $R_7$ is benzyloxycarbonyl or methansulfonyl.

Similarly, preferred compounds of formula II are those wherein $A_1$—$R_5$ is L-tryptophanyl, L-tyrosinyl or L-O-methyl tyrosinyl.

Also preferred are compounds of formula II wherein $R_1$ and $R_2$ are independently selected from the group consisting of H, arylalkyl and branched alkyl. Especially preferred are compounds wherein one of $R_1$ and $R_2$ is hydrogen and the other is benzyl, 2-naphthylmethyl, or branched alkyl.

In preferred compounds of formula II, n is 1. A preferred value for q is 4. Also preferred are compounds of formula II wherein R is hydrogen and $R_5$ is hydroxy.

Still another group of preferred compounds of formula II is that wherein $R_6$ is phenylmethoxycarbonyl or $A_2$—$R_7$, wherein $A_2$ is an α-amino acyl radical derived from a natural α-amino acid in the R or S chiral form, preferably lysine, ε-CBZ lysine, arginine, isoleucine, leucine, valine, phenylalanine, alanine, glycine or tyrosine, and $R_7$ is benzyloxycarbonyl or methansulfonyl.

This invention also relates to the use of the compounds of formula I as endothelin converting enzyme inhibitors, and especially to the use of compounds of formula II as endothelin converting enzyme inhibitors.

In another aspect, the present invention relates to a pharmaceutical composition comprising a compound of formula II in a pharmaceutically acceptable carrier.

BRIEF DESCRIPTION OF THE FIGURES

FIGS. 3, 4, 5 and 6 are graphs showing the effects of four compounds of the invention (identified below) on ischemia/hypoxia-induced BET-1 release in isolated perfused guinea pig lungs.

DETAILED DESCRIPTION

Figure 1:
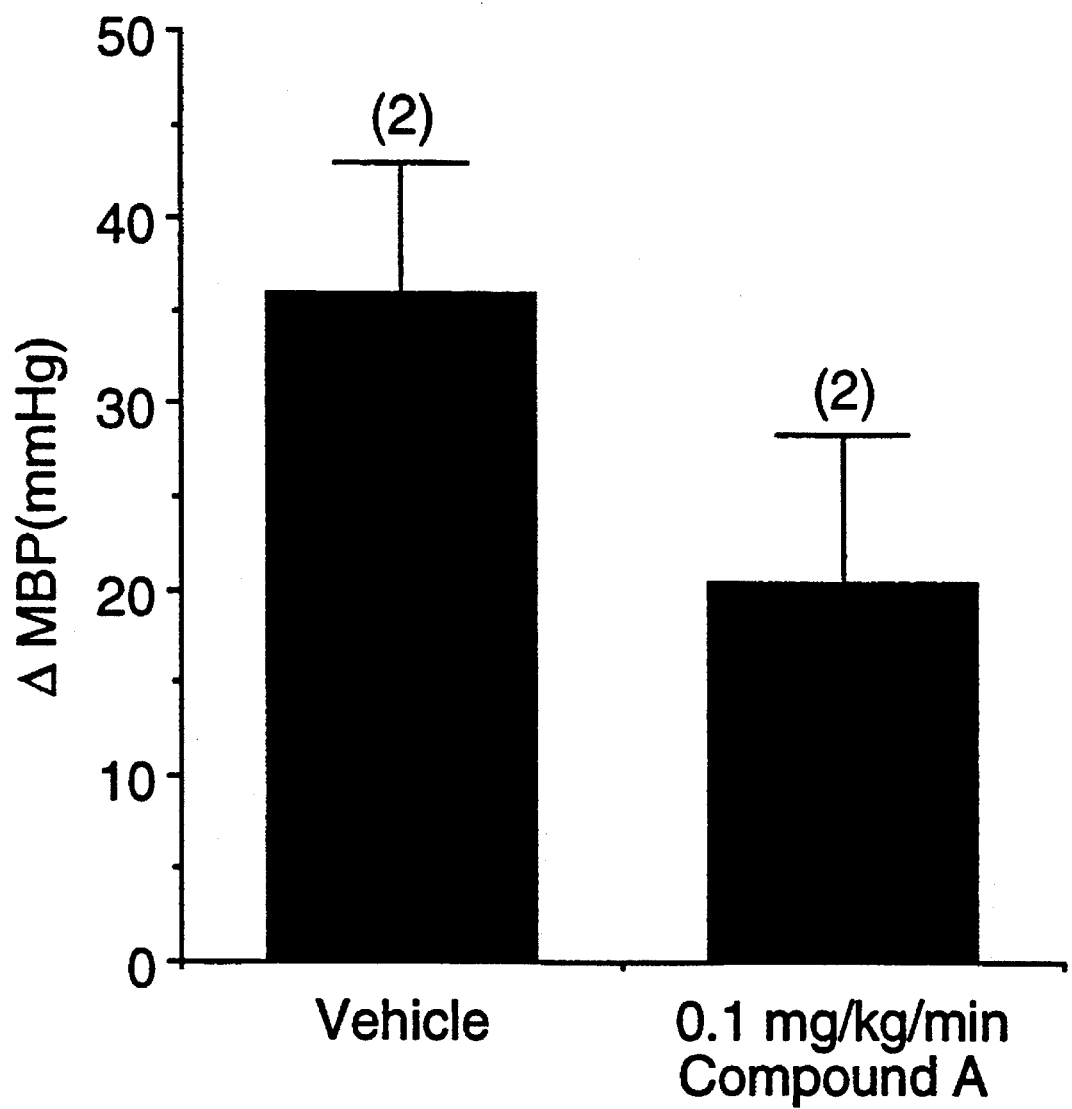
FIGS. 1 and 2 are graphs showing the effect of two compounds of the invention (identified below) on pressor responses to BET-1 in anesthetized rats.

As used herein, the term "divalent α-aminoacyl radical" refers to a radical having the structure

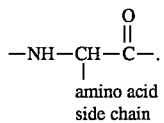
amino acid side chain

Similarly, the term "radical of an α-aminoacyl derivative" refers to a radical of the structure

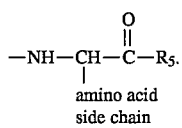
amino acid side chain

The α-aminoacyl radicals and α-aminoacyl derivatives are derived from natural α-amino acids or esters in the R or S chiral form.

As used herein, the term "alkyl" means straight or branched alkyl chains of 1 to 8 carbon atoms, "alkoxy" means alkoxy groups having 1 to 6 carbon atoms, and "alkenyl" means straight or branched carbon chains of 1 to 8 carbon atoms having one or more double bonds in the chain, conjugated or unconjugated.

"Cycloalkyl" means saturated carbocyclic rings of 3 to 6 carbon atoms. "Heterocycloalkyl" means saturated rings of 3 to 6 members wherein 1 to 3 ring members can be independently selected from the groups consisting of sulfur, oxygen and nitrogen, for example tetrahydrofuranyl, thiopyranyl, morpholinyl, pyrrolidinyl, piperidinyl or tetrahydrothiophenyl "Alkanoyloxymethylene" means a group having the formula lower alkyl-C(O)—O—$CH_2$—.

As used herein, "aryl" means a phenyl, indanyl, naphthyl or tetrahydronaphthyl ring with one or more substituents selected from the group consisting of H, alkyl, —OH, alkoxy, carboxy, halo, aminoalkyl, carbamyl, —$NO_2$, trifluoromethyl, morpholinecarbonyl, phenyl, phenoxy, benzyloxy and phenylthio, or wherein adjacent alkyl and alkoxy substituents on a phenyl ring form a five or six-membered ring, such as dihydrobenzo-furanyl.

"Heteroaryl" represents furanyl, thienyl, pyrrolyl, or their benzo-fused forms, such as indolyl and benzofuranyl, optionally substituted as described for aryl.

"Halo" refers to fluorine, chlorine, bromine or iodine radicals.

Compounds of the invention have at least one asymmetrical carbon atom and therefore all isomers, including diastereomers and rotational isomers are contemplated as being part of this invention. The invention includes d and l isomers in both pure form and in admixture, including racemic mixtures. Isomers can be prepared using conventional techniques, either by reacting enantiomeric starting materials or by separating isomers of a compound of formula I or II. Isomers may also include geometric isomers, e.g. when a double bond is present. All such geometric isomers are contemplated for this invention.

Those skilled in the art will appreciate that for some compounds of formula I or II, one isomer will show greater pharmacological activity than another isomer.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous $NaHCO_3$. The free base form differs from its respective salt form somewhat in certain physical properties, such as solubility in polar solvents, but the salt is otherwise equivalent to its respective free base forms for purposes of the invention.

Compounds of the invention which are acidic form pharmaceutically acceptable salts with inorganic and organic bases. Examples of such salts are the alkali metal and alkaline earth salts, such as the lithium, sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formulas I and II are prepared by methods known to those skilled in the art, using starting materials which are commercially available or readily prepared using known methods. Following are descriptions which exemplify two processes for preparing the compounds of this invention.

Process A:

Compounds of formula I wherein one of $R_3$ and $R_4$ is hydrogen and the other is as defined above, and the remaining variables are as defined above, can be prepared according to the following reaction scheme, wherein $R_3$ is exemplified as hydrogen.

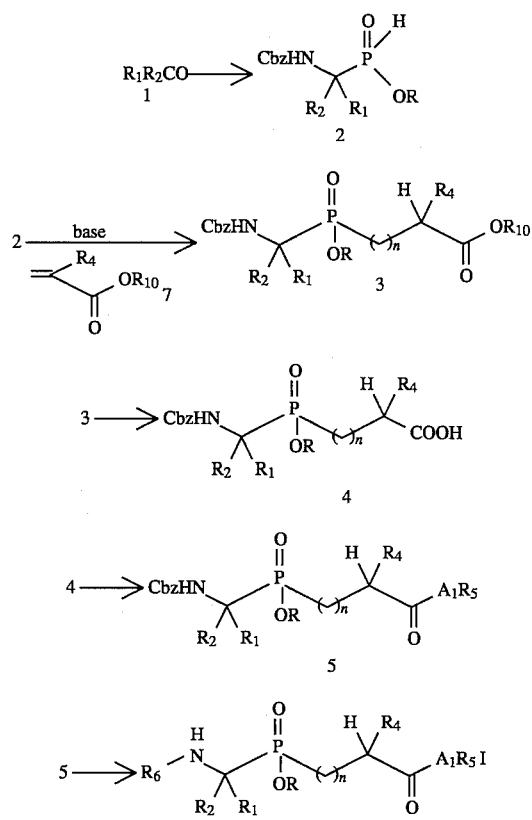

Phosphinic acids 2, wherein $R_1$, $R_2$ and R are as defined above and Cbz is benzyloxycarbonyl, are known compounds and can be prepared from carbonyl compounds 1 by known methods. Alternatively, the amino group can be protected by other suitable protecting groups, e.g., tert-butoxycarbonyl. The phosphinic acids 2 are conceded to the conjugate addition products 3, wherein n is 1, by known methods or by a variation of known methods where the phosphinic acids 2 are deprotonated with one equivalent of a suitable base such as NaH and reacted in a solvent such as tetrahydrofuran (THF) with an acrylate 7, wherein $R_{10}$ is a carboxylic acid protecting group such as methyl, ethyl, benzyl, 2-trimethylsilylethyl or 3,4-dimethoxybenzyl. Compounds 3 are deprotected to give acids 4 using standard methodology. Acids 4 are coupled to an amino acid ester such as tryptophan methyl ester using a suitable coupling agent such as 1,1'-carbonyldiimidazole in an organic solvent such as dimethylformamide (DMF) to give compounds 5. Compounds 5 can be further elaborated to compounds I by standard peptide coupling procedures and protecting group manipulations where necessary.

Process B:

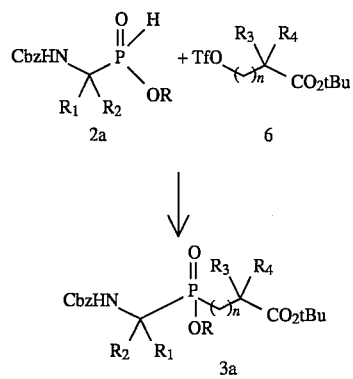

Phosphinic acid esters 2a, wherein R, $R_1$, $R_2$, $R_3$ and $R_4$ are as defined above, are deprotonated with a suitable base such as lithium diisopropylamide (LDA) in a suitable solvent such as THF at low temperature, then are reacted with a triflate (Tf) of formula 6 to give a compound 3a. Compound 3a can be elaborated into compounds of formula I by the methods described for Process A.

Starting materials for the above processes are known in the art or can be prepared by known methods, some of which are exemplified in the Preparations below.

The present invention relates to a method of inhibiting ECE, which method comprises administering to a mammal in need of such treatment an ECE inhibitory effective amount of a compound of formula I of this invention. The compound of formula I is preferably administered in a pharmaceutically acceptable carrier, especially a pharmaceutical carrier suitable for oral administration.

In addition to the method of treatment aspect, novel compounds of formula II are also claimed, and therefore the present invention also relates to pharmaceutical compositions comprising an ECE inhibitory effective amount of a compound of formula II in a pharmaceutically acceptable carrier The compounds of formula I or II can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, antioxidants, lubricants, flavorings, thickeners, coloring agents, emulsifiers and the like. Similar pharmaceutical compositions can also be prepared comprising compounds of formula I.

The daily ECE inhibitory dose of a compound of formula I or II is about 0.1 to about 100 mg/kg of body weight per day, preferably about 10 mg/kg. For an average body weight of 70kg, the dosage level is therefore from about 7 mg to about 7 g of drug per day, preferably about 700 mg, given in a single dose or 2–4 divided doses. The exact dose, however, is determined by the attending clinician and is dependent on the potency of the compound administered, the age, weight, condition and response of the patient.

Following are preparations of starting materials and examples of processes for obtaining compounds of formulae I and II. In the preparations and examples, abbreviations are used as follows: R.T. is room temperature, sat'd is saturated, aq. is aqueous, EtOAc is ethyl acetate, $Et_2O$ is diethyl ether, EDC is 1-(3-dimethylaminopropyl)-3-ethylcarbodiimide hydrochloride, HOBT is 1-hydroxybenzotriazole hydrate, HOAc is acetic acid, Ms is methanesulfonyl, Cbz is carbobenzyloxy and Boc is t-butoxycarbonyl.

Preparation 1

4-((1,1-Dimethylethoxycarbonyl)aminomethyl)benzoic acid

To an ice-cold solution of 4-(aminomethyl)benzoic acid (7.6 g, 50 mmol) in 1M NaOH (50 ml), 1,4-dioxane (100 ml) and H$_2$O (50 ml) add di-t-butyl dicarbonate (12.0 g, 55 mmol) with rapid stirring. Stir the mixture for 1 h, then evaporate to low volume. Cool the resulting aq. solution in an ice-bath, cover with a layer of EtOAc (250 ml) and acidify with conc. HCl. Extract the aq. layer with EtOAc (2×100 ml), wash the combined EtOAc layers with sat'd NaCl, dry (MgSO4), filter and evaporate to dryness. Recrystallize (EtOAc/hexanes) the residue to obtain the title compound (7.78 g, 62%) as needles. Anal. calcd for C$_{13}$H$_{17}$NO$_4$: C, 62.14; H, 6.82; N, 5.57%. Found: C, 62.18; H, 6.82; N, 5.55%. FAB MS m/z 252 (M+H)$^+$.

Preparation 2

(4-Methoxyphenyl)ethanal

To a stirred solution of methyl 4-methoxyphenylacetate (45.0 g) in toluene (250 ml) cooled to −78° C., add a 1.5M solution of DIBALH in toluene (167 ml) over 5 h, maintaining the reaction temperature at −78° C. Stir for an additional 0.5 h, then pour into 1:1 ice/1M HCl (1500 ml) and Et$_2$O (500 ml). Stir the slurry for 1 h, separate the layers and extract the aq. layer with Et$_2$O (2×500 ml). Wash the combined organic layers with sat'd NaHCO$_3$ (500 ml) and sat'd NaCl, dry (MgSO$_4$), filter and evaporate to give an oil. Perform bulb-to-bulb distillation (100°–130° C., 1 mmHg) to obtain the title compound (33.9 g, 90%) as a colorless liquid. $^1$H Nmr (CDCl$_3$) δ9.71 (1H, t, J=2.4 Hz), 7.12 (2H, m), 6.89 (2H, m), 3.79 (3H, s) 3.61 (2H, m).

Using appropriate starting materials and essentially the same procedure the following compounds are prepared:

Prep. 2A: [(4-Phenylmethoxy)phenyl]ethanal $^1$H Nmr (CDCl$_3$) δ9.76 (1H, t, J=2.4 Hz), 7.49–7.37 (5H, m), 7.17 (2H, m), 7.02 (2H, m), 5.10 (2H, s), 3.66 (2H, m).

Preparation 3

N-(Triphenylmethyl)-(4-methoxyphenyl)acetaldimine

To a stirred slurry of (4-methoxyphenyl)ethanal (28.92 g, 0.193 mol) and MgSO$_4$ (20 g) in CH$_2$Cl$_2$ (100 ml), add a solution of tritylamine (50.0 g, 0.193 mol) in CH$_2$Cl$_2$ (180 ml) over 10 min. After 1 h, filter the mixture and evaporate the filtrate to dryness to obtain the title compound as a viscous oil. $^1$H Nmr (CDCl$_3$) δ7.36–7.15 (16H, m), 7.15 (2H, m), 6.83 (2H, m), 3.77 (3H, s), 3.73 (2H, m).

Using appropriate starting materials and essentially the same procedure, the following compounds are prepared:

Prep. 3A: N-(Triphenylmethyl)-[(4-phenylmethoxy)phenyl]acetaldimine $^1$H Nmr (CDCl$_3$) δ7.46–7.20 (21H, m), 7.13 (2H, m), 6.93 (2H, m), 5.08 (2H, s), 3.75 (2H, m).

Preparation 4

1-Amino-2-(4-methoxy)phenylethyl phosphinic acid

Prepare neat bis(trimethylsilyl)phosphonite from hexamethyldisilazane (61 ml, 0.29 mol) and ammonium hypophosphite (24 g, 0.29 mol), and dilute with CH$_2$Cl$_2$ (100 ml). To a stirred ice-cold solution of Preparation 3 in CH$_2$Cl$_2$ (250 ml) under N$_2$, add the solution of bis(trimethylsilyl)phosphonite via canula. Allow the reaction mixture to reach R.T. After 20 h, cool the reaction mixture in an ice bath and quench with 85% EtOH (250 ml). After 4 days, collect the precipitate, wash with 85% EtOH, air-dry and dry in vacuo to obtain the title compound (23.1 g, 56% as a white powder. FAB MS m/z 216 (M+H)$^+$.

Using appropriate starting materials and essentially the same procedure, the following compounds are prepared:

Prep. 4 A: 1-Amino-2-(4-phenylmethoxy)phenylethyl phosphinic acid $^1$H Nmr (DMSO-d6+TFA) δ8.21 (3H, bs), 7.41–7.28 (5H, m), 7.21 (2H, m), 7.03 (1H, d, J=555.5 Hz), 6.95 (2H, m), 5.06 (2H, s), 3.51 (1H, bm), 3.04 (1H, m), 2.81 (1H, td, J=14.4, 8.9 Hz). FAB MS 292.1 (M+H)$^+$.

Preparation 5

2-(4-Methoxy)phenyl-1(R,S)-[N-[(phenylmethoxy)carbonyl]]aminoethyl phosphinic acid To a stirred solution of Preparation 4 (21.5 g, 0.10 mol) in ice-cold 1M NaOH (100 ml), separately add benzyl chloroformate (16 ml, 0.11 mol) and 1M NaOH (100 ml) and stir for 6 h. Add additional benzyl chloroformate (8 ml, 0.05 mol) and adjust the reaction mixture to pH 9 by addition of 1M NaOH. After 4 h, acidify the reaction mixture to pH 1 by addition of conc. HCl. Collect the precipitate, wash with H$_2$O, air-dry, then dry in vacuo to obtain the title compound (34.8 g, 100%) as a white powder. FAB MS m/z 350 (M+H)$^+$.

Using essentially the same procedure the following compounds are prepared:

Prep. 5A: 1(R,S)-[N-[(Phenylmethoxy)carbonyl]]amino-2-(4-phenylmethoxy)phenylethyl phosphinic acid $^1$H Nmr (DMSO-d6) δ7.71 (1H, d, J=9.1 Hz), 7.46–7.28 (8H, m), 7.21 (2H, m), 7.17 (2H, d, J=8.6 Hz), 6.92 (2H, d, J=8.7 Hz), 6.87 (1 H, d, J=533.5 Hz), 5.07 (2H, s), 4.96 (2H, m), 3.79 (1H, m), 2.95 (1H, dt, J=14.4, 4.0Hz), 2.69 (1H, td, J=14.4, 8.2 Hz). FAB MS m/z 426.1 (M+H)$^+$.

Preparation 6

P(R,S)-2-Phenyl-1(R)-[(phenylmethoxy)carbonyl]aminoethyl phosphinic acid methyl ester To a stirred solution of 2-phenyl-1(R)-[(phenylmethoxy)carbonyl]aminoethylphosphinic acid (See Baylis, et al., *J. Chem. Soc. Perkin Trans.*, 1 (1984), p. 2845)(3.12 g, 9.77 mmol) in ice-cold 10:11,4-dioxane/MeOH (150 ml), add excess CH$_2$N$_2$ in ether. Add CH$_3$OH to disperse the resulting suspension and allow the reaction mixture to reach R.T. Destroy excess Ch$_2$N$_2$ by addition of HOAc. Evaporate the reaction mixture to a syrup, then take up in EtOAc (100 ml), wash with sat'd NaHCO$_3$ (50ml) and sat'd NaCl, dry (MgSO$_4$), filter and evaporate to obtain the title compound (2.72 g, 84%) as a syrup which crystallizes on standing. Mixture of diastereomers at phosphorous. $^1$H Nmr (CDCl$_3$) δ 7.32–7.17 (10H, m), 7.01* (0.4H, d, J=558.8 Hz) and 6.99* (0.6H, d, J=559.1 Hz), 5.18* (0.6H, d, J=9.2 Hz) and 5.09* (0.4H, d, J=9.0 Hz), 5.00* (0.8H, s) and 4.98* (1.2H, s),4.21 (1H, m), 3.73* (1.8H, d, J=11.4 Hz) and 3.72* (1.2 Hd, J=11.4 Hz), 3.15 (1H, m), 2.91 (1H, m). * Diastereomeric signals.

Using appropriate starting materials and essentially the same procedure the following compound is prepared:

Prep. 6A: P(R,S)-1R,S)-[(Phenylmethoxy)carbonyl]amino-2-(4-phenylmethoxy)phenylethyl phosphinic acid methyl ester Mixture of diastereomers at phosphorous. $^1$H Nmr (CDCl$_3$) δ7.44–7.21 (10H, m), 7.15–7.06 (2H, m), 7.04* (0.5H, d, J=556.0 Hz), 7.02* (0.5H, d, J=556.0 Hz), 6.88 (2H, m), 5.08–4.97 (5H, m), 4.21 (1H, m), 3.76* (1.5H, d, J=11.9 Hz), 3.74* (1.5H, d, J=11.9 Hz),3.12 (1H, m), 2.89 (1H, m). * Diastereomeric signals.

Preparation 7

P(R,S)-2-(4-Methoxy)phenyl-1(R,S)-[(phenylmethoxy)carbonyl]aminoethyl phosphinic acid methyl ester To a stirred ice-cold suspension of Preparation 5 (6.00 g, 17.2 mmol) and 4-dimethylaminopyridine (42 mg, 0.34 mmol) in 6:1 THF/CH$_3$OH (60 ml), add EDC (3.62 g, 18.9 mmol). After 20 min., remove the ice bath, stir the reaction mixture for 4 h, then evaporate to a syrup. Partition the syrup between EtOAc (60 ml) and 1M HCl (60 ml). Extract the aq. layer with EtOAc (2×60 ml) and wash the combined organic layers with H$_2$O (100 ml), 10% NaHCO$_3$ (100 ml) and sat'd NaCl, then dry (MgSO$_4$), filter and evaporate to obtain the title compound (5.40 g, 87%) as a syrup. FAB MS m/z 364.2 (M+H)$^+$.

Preparation 8 t-Butyl Cyclopentanecarboxylate

Cool a metal bomb in a CO$_2$-acetone bath and charge with isobutylene (150 ml), cyclopentanecarboxylic acid (29.4 g, 0.26 mol), t-butanol (4 ml) and H$_2$SO$_4$ (1 ml). Remove the bomb from the cold-bath, seal and stir for 3 days. Cool the bomb in a CO$_2$-acetone bath, open to the atmosphere and evaporate isobutylene under a stream of N$_2$ while allowing the reaction mixture to attain R.T. Add Et$_2$O (300 ml) and wash the mixture with sat'd NaHCO$_3$ (300 ml) and sat'd NaCl, then dry (MgSO$_4$), filter and concentrate to obtain a colorless oil (41.5 g, 95%) which is used without further purification. $^1$H Nmr (CDCl$_3$) δ2.58 (1H, m), 1.90–1.35 (8H, m), 1.39 (9H, s).

Preparation 9 t-Butyl 1-hydroxymethylcyclopentanecarboxylate

To a stirred, ice-cold solution of diisopropylamine (34 ml, 0.24 mol) in THF (800 ml), add a solution of n-BuLi in hexanes (2.5M, 100 ml, 0.25 mol). After 0.5 h, cool the mixture to −78° C. and add a solution of Preparation 8 (41 g, 0.24 mol) in THF (100 ml) via canula under N$_2$ over 0.5 h. After 1 h, to the stirred −78° C. solution, add paraformaldehyde (36 g, 5 equiv.), stir at −78° C. for 1 h, then remove the cold bath. Stir the resulting gel-like suspension for 4 h, then quench with sat'd NH$_4$Cl (800 ml). Extract with EtOAc (2×800 ml), wash the combined EtOAc extracts with 1M HCl and sat'd NaCl, dry (MgSO$_4$), filter and concentrate. Distill the crude product to obtain the title compound (42.5 g, 89%) as a colorless liquid. B.p. 100°–110° (0.4 mmHg). $^1$HNmr(CDCl$_3$)δ2.58(1H,m),1.90–1.35(8H,m),1.39(9H,s).

Preparation 10 t-Butyl 1-[(trifluoromethanesulfonyl)oxy]methylcyclopentanecarboxylate

To a stirred solution of pyridine (10 ml, 124 mmol) in CH$_2$Cl$_2$ (75 ml) cooled to −78° C. under N$_2$, add a solution of triflic anhydride (10 g, 35.5 mmol) in CH$_2$Cl$_2$ (10 ml) dropwise via an addition funnel. After 10 min, add, dropwise, a solution of Preparation 9 (4.73 g, 23.7 mmol) in CH$_2$Cl$_2$ (20 ml). Stir the resulting reaction mixture at −78° C. for 0.5 h, then remove the cold-bath. When the reaction mixture reaches R.T., pour into hexanes (500 ml), wash with 1 m HCl (3×200 ml), H$_2$O (200 ml), sat'd NaHCO$_3$ (200 ml) and sat'd NaCl, then dry (MgSO$_4$), filter and evaporate to dryness. The resulting reddish oil (7.34 g, 93%) solidifies on storage at freezer temperature, and is used without further purification. $^1$H Nmr (CDCl$_3$) δ4.51 (2H, s), 2.11–2.05 (2H, m), 1.79–1.54 (4H, m), 1.44 (9H, s).

Preparation 11

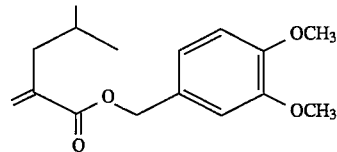

Step 1:

Add aq. formaldehyde solution (37%, 16.1 ml) to an aq. solution of (CH$_3$)$_2$NH (40%, 12.5 ml) cooled in an ice bath. Stir the mixture for 10 min, then add isobutylmalonic acid (16.7 g, 104 mmole). Allow the reaction mixture to warm to R.T., then heat at 90° C. for 1 hr. Cool the reaction mixture to R.T., acidify with 1N HCl to pH 1 and extract with Et$_2$O. Dry the Et$_2$O layer over MgSO$_4$ and concentrate under reduced pressure.

Step 2:

Cool a solution of the product of Step 1 in CH$_2$Cl$_2$ (90 ml) in an ice bath and add 3,4-dimethoxybenzyl alcohol (29.2 g, 174 mmol), dimethylaminopyridine (750 mg, 6 mmol) and a solution of DCC (30.8 g, 150 mmol) in CH$_2$Cl$_2$ (180 ml). Stir the reaction mixture at 0° C. for 1 hr, then keep in the freezer (−20° C.) for 18 hrs. Filter the reaction mixture, wash the filtrate with CH$_2$Cl$_2$, concentrate in vacuo and purify the crude product by chromatography on silica gel, eluting with 10% EtOAc in hexane to obtain 22 g (76% of theory) of the title compound. $^1$H NMR (400 MHz, CDCl$_3$) δ6.82–6.98 (m, 3H), 6.2 (s, 1H), 5.5 (s, 1H), 3.80 (s, 6H), 220 (d, J=6.7 Hz, 2H), 1.82 (m, 1H), 0.90 (d, J=6.7 Hz, 6H).

EXAMPLE 1

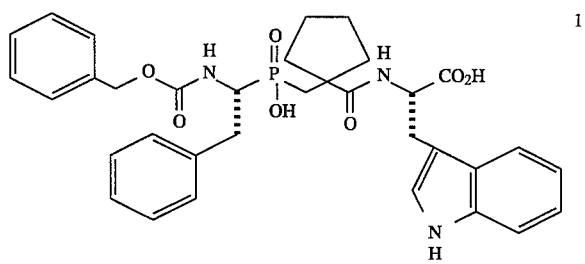

Step 1:

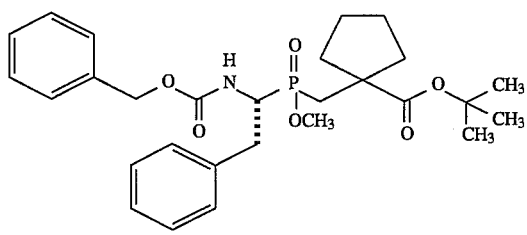
1.1

Step 2:

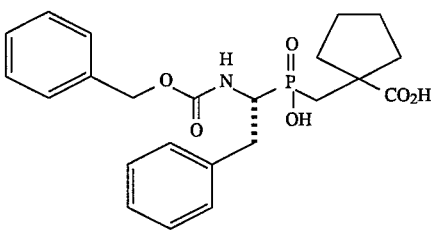
1.2

To a stirred ice-cold solution of diisopropylamine (1.93 ml, 13.8 mmol) in THF (15 ml), add a solution of n-butyllithium in hexanes (1.6M, 8.6 ml, 13.8 mmol) under $N_2$. After 15 min, cool the reaction mixture to −78° C. To this LDA solution at −78° C., add a solution of Preparation 6 (4.20 g, 12.5 mmol) in THF (25 ml) at such a rate that the temperature remains below −60° C. After the addition is complete, stir the reaction mixture for 10 min., then add a solution of Preparation 10 (4.98 g, 15.0 mmol) in THF (12 ml). Stir the reaction mixture at −78° C. for 15 min, then remove the cold-bath. After 4 h, quench the reaction mixture with sat'd $NH_4Cl$ (200 ml) and extract with EtOAc (2×200 ml). Wash the combined organic extracts with 1M HCl (400 ml), sat'd $NaHCO_3$ (400 ml) and sat'd NaCl, then dry ($MgSO_4$), filter and evaporate. Flash chromatography of the residue (3:2 EtOAc/hexanes) yields compound 1.1 (3.78 g, 59%) as a white solid. $^1H$ Nmr analysis shows a 2:1 mixture of diastereomers at phosphorous. Major diastereomer; $^1H$ Nmr (CDCl$_3$) δ7.38–7.07 (10H, m), 5.06–4.95 (3H, m), 4.28 (1H, m), 3.64 (3H, d, J=10.3 Hz), 3.32 (1H, m), 2.82 (1H, m), 2.31–2.03 (4H, m), 1.83–1.50 (6 H, s), 1.48 (9H, s). Minor diastereomer; $^1H$ Nmr (CDCl$_3$) δ7.38–7.07 (10H, m), 5.22 (1H, d, J=9.6 Hz), 5.06–4.95 (2H, m), 4.28 (1H, m), 3.74 (3H, d, J=10.3 Hz), 3.22 (1H, 2.82 (1H, m), 2.31–2.03 (4H, m), 1.83–1.50 (6H, m), 1.46 (9H, s). FAB HRMS calcd for $C_{28}H_{39}NO_6P$ 516.2515 (M+H)$^+$. Found 516.2532.

Using appropriate starting materials and essentially the same procedure the following compounds are prepared:

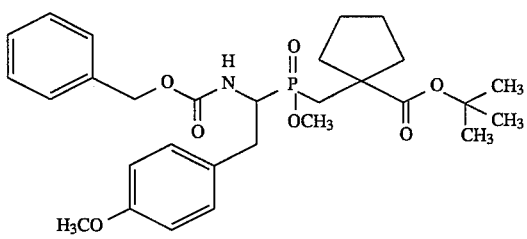
1.1A $^1H$ Nmr (CDCl$_3$) δ7.36–7.08 (7H, m), 6.84–6.76 (2H, m), 5.21–4.92 (3H, m), 4.23 (1H, m), 3.79 (3H, s), 3.74–3.59 (3H, m), 3.28–3.09 (1H, m), 2.80 (1H, m), 2.30–1.99 (4H, m), 1.78–1.50 (6H, m), 1.46 (9H, s).

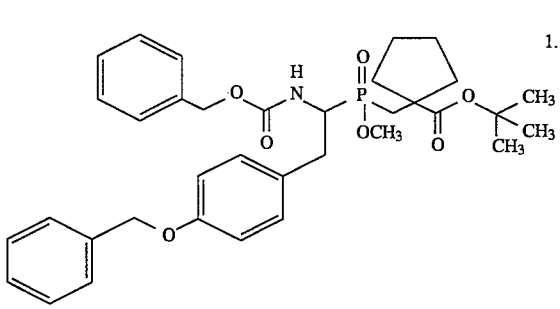
1.1B

FAB MS m/z 622.4 (M+H)$^+$.

Method (i): To a stirred ice-cold solution of Example 1.1 (7.50 g, 14.6 mmol) in $CH_2Cl_2$ (120 ml), add $CF_3CO_2H$ (20 ml). After 1 h, add $CF_3CO_2H$ (20 ml) at hourly intervals until TLC shows no starting material (ca 4.5 h). Evaporate the reaction mixture to a syrup, then take up in $CH_2Cl_2$ and evaporate to dryness (2×). Crystallize the residue from EtOAc to obtain compound 1.2 (5.77 g, 89%). [α]$_D$-52° (c 0.605, DMF). Anal. calcd for $C_3H_{28}NO_6P$: C, 62.02; H, 6.34; N, 3.14; P, 6.95%. Found: C, 62.24; H, 6.09; N, 3.25; P, 6.97%.

Method (ii): Dissolve compound 1.1 (2.144 g, 4.16 mmol) in 4M HCl/1,4-dioxane (45 ml). Stir the reaction mixture for 4 h, then add additional 4M HCl/1,4-dioxane (45 ml). After 6 h, evaporate the reaction mixture to a syrup and take up in 1M NaOH (150 ml). Wash the aq. solution with EtOAc (2×100ml) and acidify the aq. layer to pH 1 with conc. HCl. Extract the aq. emulsion with EtOAc (150 ml), then saturate the aq. layer with NaCl and extract with EtOAc (350 ml). Wash the combined EtOAc layers with sat'd NaCl, dry (MgSO$_4$), filter and evaporate to dryness to obtain compound 1.2 (1.810 g, 98%) as a white solid.

Using appropriate starting materials and essentially the same procedure described in Method (ii) the following compounds are prepared:

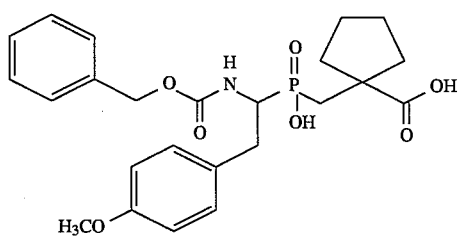
1.2A

FAB HRMS Calcd for $C_{24}H_3NO_7P$: 476.1838; found 476.1850.

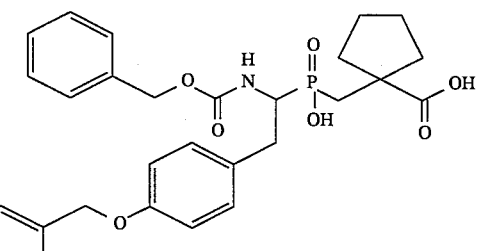
1.2B

FAB MS m/z 552.2 (M+H)$^+$.

Step 3:

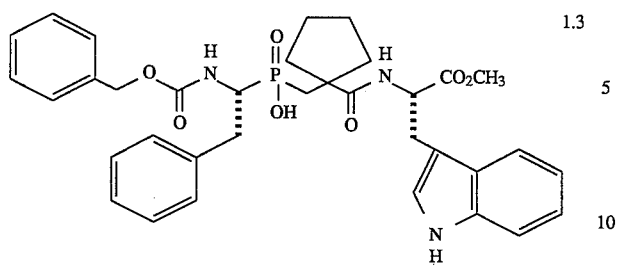

1.3

To a stirred ice-cold solution of Example 1.2 (1.505 g, 3.38 mmol) in DMF (18 ml), add 1,1'-carbonyldiimidazole (0.823 g, 5.07 mmol). After 0.5 h, allow the reaction mixture to warm to R.T., and after a further 1 h, add L-tryptophan methyl ester hydrochloride (1.72 g, 6.75 mmol) followed by N.-methylmorpholine (0.74 ml, 6.7 mmol). Stir the reaction mixture for 48 h, then partition between EtOAc (200 ml) and 1M HCl (200 ml). Saturate the aq. layer with NaCl and extract with EtOAc (200 ml). Wash the combined EtOAc layers several times with $H_2O$, once with sat'd NaCl, then dry ($MgSO_4$), filter and evaporate. Flash chromatography of the residue (1:24 $MeOH/CH_2Cl_2$ then 1:2:47 $CH_3CO_2H/MeOH/CH_2Cl_2$) yields compound 1.3 (1.740 g, 80%) as a beige foam. FAB HRMS calcd for $C_{35}H_{41}N_3O_7P$: $(M+H)^+$ 646.2682; found 646.2698.

Using appropriate starting materials and essentially the same procedure the following compounds are prepared:

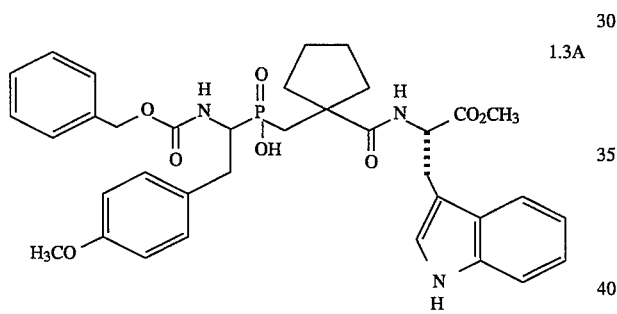

1.3A

FAB HRMS Calcd for $C_{36}H_{43}N_3O_8P$: 676.2788 $(M+H)^+$; found 676.2778.

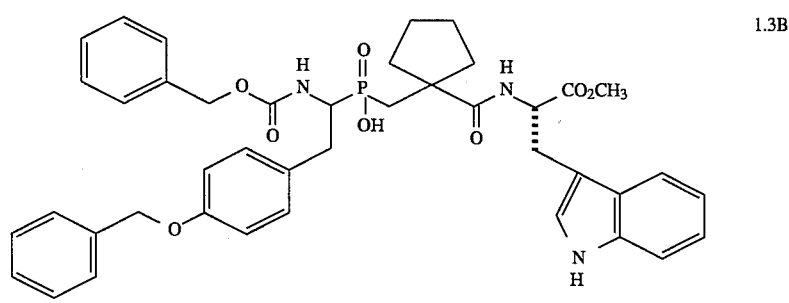

1.3B

FAB MS m/z 752.4 $(M+H)^+$.

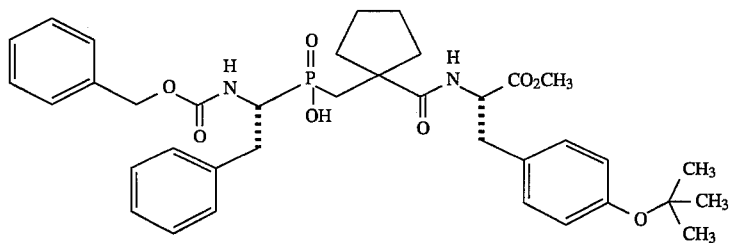

FAB MS m/z 679 (M+H)⁺

Step 4:

Stir a mixture of Example 1.3 (200 mg, 0.31 mmol) and LiOH.H$_2$O (33 mg, 0.79 mmol) in 3:2 CH$_3$OH/H$_2$O (5 ml) at R.T. for 4 h. Concentrate the reaction mixture in vacuo and acidify the resulting aq. suspension to pH 1 with dilute HCl. Filter the precipitate, wash it with H$_2$O, air-dry, then dry in vacuo to give compound 1 (182 mg, 93%) as a white solid. Anal. calcd for C$_{34}$H$_{38}$N$_3$O$_7$P.H$_2$O: C, 62.86; H, 6.21; N, 6.47; P, 4.77%. Found: C, 63.19; H, 5.92; N, 6.40; P, 4.72%. FAB MS m/z 632 (M+H)⁺.

Using appropriate starting materials and essentially the same procedure the following compounds are prepared:

1A

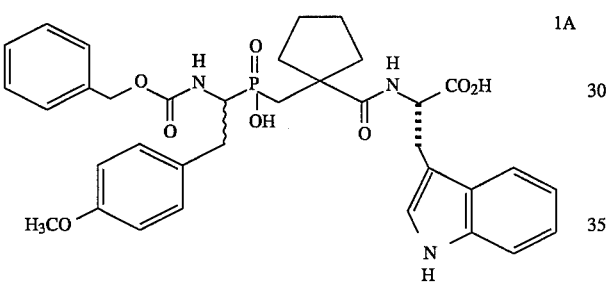

FAB HRMS Calcd for C$_{35}$H$_{41}$N$_3$O$_8$P: 662.2631 (M+H)⁺; found 662.2648.

1B

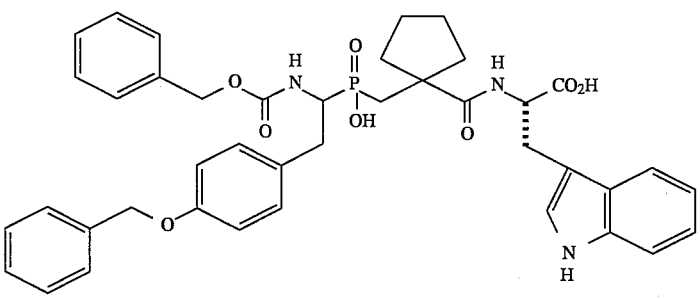

Compound 1B is a mixture of 2 diastereomers. Anal. calcd for C$_{41}$H$_{44}$N$_3$O$_8$P.1.2H$_2$O: C, 64.84; H, 6.16; N, 5.53; P, 4.08%. Found: C, 64.61; H, 5.81; N, 5.44; P, 3.97%.

Using appropriate starting materials and following the procedures of Example 1, Steps 1-4, the following compound can also be prepared as a mixture of 2 diastereomers:

1C

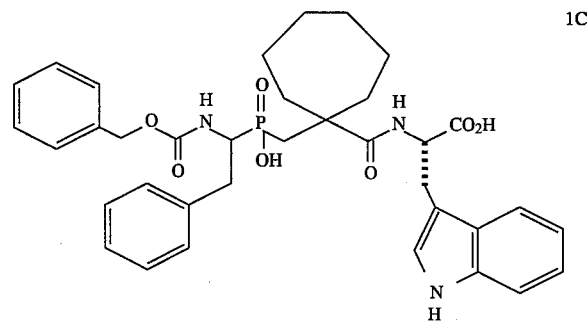

¹H Nmr (DMSO-d6) δ8.04–7.94 (1H, m), 7.60–7.54 (1H, m), 7.58–6.96 (15H, m), 4.98–4.88 (2H, m), 4.58–4.42 (1H, m), 3.87–3.74 (1H, m), 3.21–3.16 (3H, m), 2.76–2.64 (1H, m), 2.16–1.13 (14H, m).

EXAMPLE 2

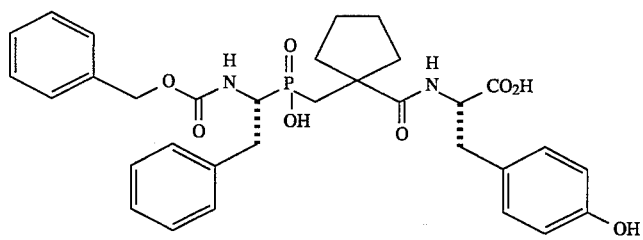

2

To a stirred solution of Example 1.3C (150 mg, 0.22 mmol) in CH$_2$Cl$_2$ (4 ml), add CF$_3$CO$_2$H (8 ml). After 2 h, evaporate the reaction mixture to dryness to obtain the methyl ester of the title compound as a foam (135 mg, 99%). FAB MS 623 (M+H)$^+$. To this ester (130 mg, 0.21 mmol) in CH$_3$OH (3 ml), add LiOH.H$_2$O (37 mg, 0.88 mmol). Stir the reaction mixture overnight, then concentrate in vacuo to remove CH$_3$OH. Dilute the resulting aq. mixture with H$_2$O (10 ml), wash with EtOAc (10 ml), acidify to pH 1 with 1M HCl and extract with EtOAc (50 ml). Saturate the aq. layer with NaCl and extract with EtOAc (50 ml). Wash the combined EtOAc extracts with sat'd NaCl, dry (MgSO$_4$), filter and evaporate to dryness to obtain compound 2 (107 mg, 84%). FAB MS m/z 609 (M+H)$^+$.

by addition of CH$_3$CO$_2$H, wash the mixture with sat'd NaHCO$_3$ (50 ml) and sat'd NaCl (50 ml), dry (MgSO$_4$), filter and evaporate to give compound 3.1 as a foam (1.78 g, 96%). FAB HRMS calcd for C$_{36}$H$_{43}$N$_3$O$_7$P (M+H)$^+$ 660.2839. Found 660.2812.

EXAMPLE 3

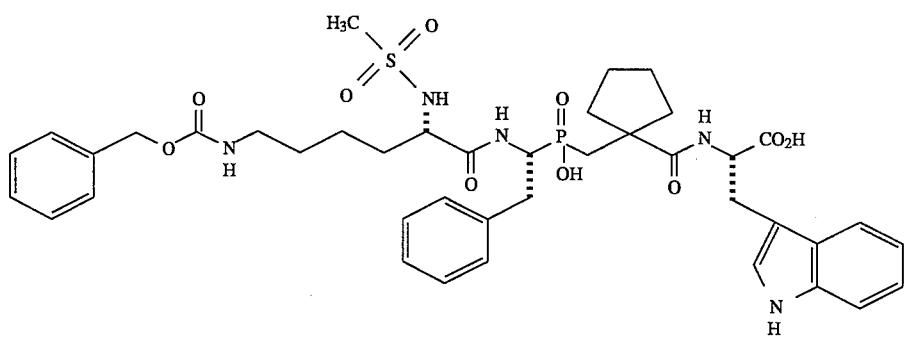

3

Step 1:

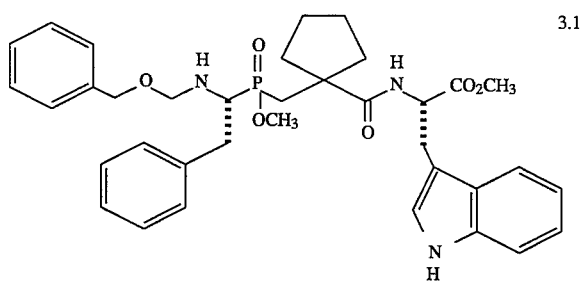

3.1

Treat a solution of Example 1.3 (1.80 g, 2.8 mmol) in EtOAc (50 ml) with a solution of Ch$_2$N$_2$ in Et$_2$O until the yellow color persists. Add a few drops of CH$_3$CO$_2$H to decompose the excess Ch$_2$N$_2$ and wash the mixture with 1M HCl (50 ml) and sat'd NaCl (50 ml). Treat the organic layer with excess Ch$_2$N$_2$ in Et$_2$O. Decompose the excess Ch$_2$N$_2$ Using appropriate starting materials and essentially the same procedure the following compounds are prepared:

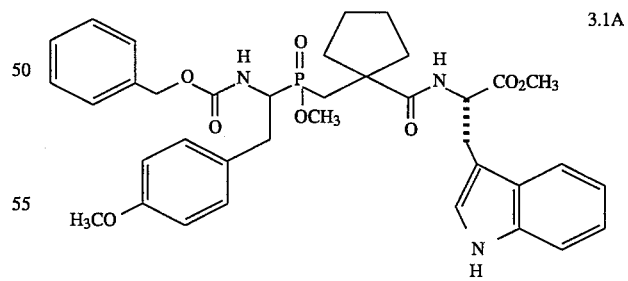

3.1A

FAB HRMS calcd for C$_{37}$H$_{45}$N$_3$O$_8$P (M+H)$^+$ 690.2944. Found 690.2970.

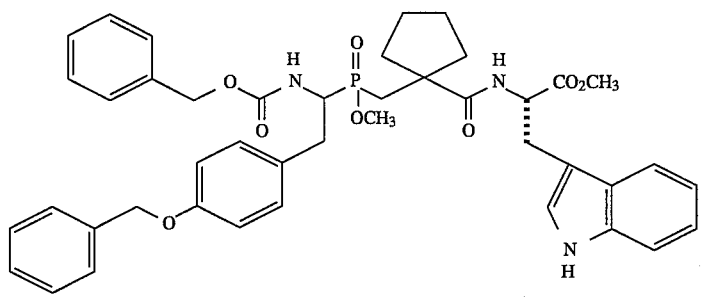

3.1B

FAB MS m/z 766.7 (M+H)⁺.

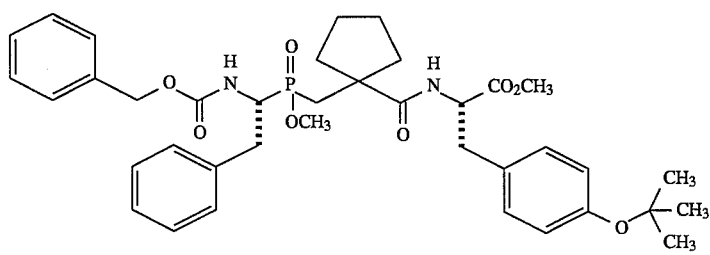

3.1C

FAB HRMS Calcd for $C_{38}H_{50}N_2O_8P$ (M+H)+ 693.3305. Found 693.3319.

Step 2:

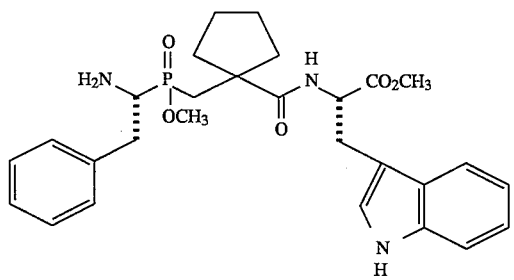

3.2

Stir a solution of Example 3.1 (1.75 g, 2.66 mmol) in CH₃OH (100 ml) containing 10% Pd/C (0.26 g) under a H₂ atmosphere for 5 h. Remove the catalyst by filtration through celite and wash the filter pad with CH₃OH. Evaporate the combined filtrate and washings to dryness to give compound 3.2 (1.34 g, 96%) as a colorless glass. $^1$H Nmr (CDCl₃) δ8.31 (1H, bs), 7.66 (1H, d, J 7.5 Hz), 7.36–7.06 (10H, m), 4.85 (1H, m), 3.59–3.41 (7H, m), 3.32–3.11 (4H, m), 2.85–2.50 (4H, bm), 2.36–1.48 (9H, m). FAB MS m/z 526 (M+H)⁺.

Using appropriate starting materials and essentially the same procedure the following compounds are prepared:

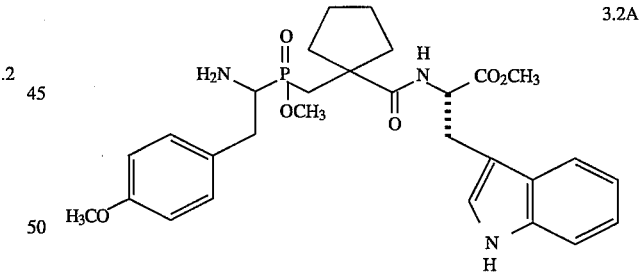

3.2A

FAB HRMS calcd for $C_{29}H_{39}N_3O_6P$ (M+H)⁺ 556.2576. Found 556.2586.

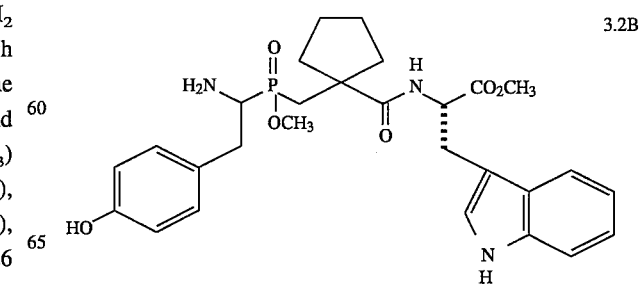

3.2B

FAB MS m/z 542.2 (M+H)⁺.

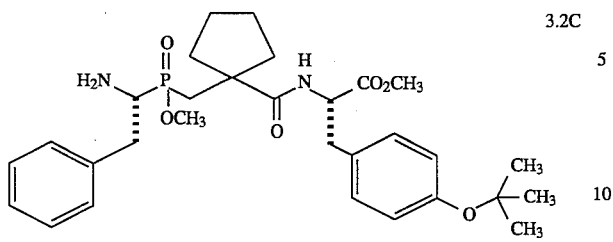

3.2C

FAB MS 559.4 (M+H)⁺.

Step 3:

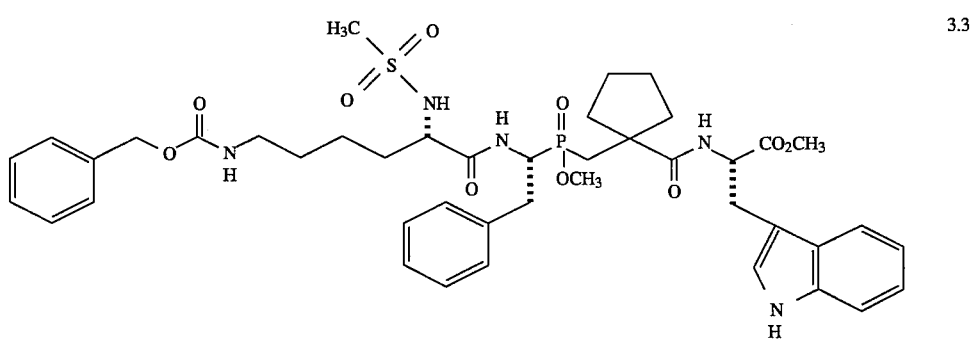

3.3

To a stirred solution of Example 3.2 (3.00 g, 5.85 mmol), N^ε-phenylmethoxycarbonyl-N^α-methylsulfonyl-(S)-lysine (ε-CBZ-α-Ms-Lys) (2.09 g, 5.85 mmol) and HOBT (0.87 g, 6.43 mmol) in CH₂Cl₂ (80 ml), add EDC (1.23 g, 6.43 mmol). After 48 h, pour the reaction mixture into 1M HCl (200 ml) and extract with EtOAc (2×200 ml). Saturate the aq. layer with NaCl and extract with EtOAc (100 ml). Wash the combined organic layers with 10% NaHCO₃ (150 ml) and sat'd NaCl, then dry, filter and evaporate. Flash chromatography of the residue (1:10:10 CH₃OH/EtOAc/hexanes) affords compound 3.3 (4.02 g, 79%) as a pale yellow foam, FAB MS m/z 866.5 (M+H)⁺.

Using appropriate starting materials and essentially the same procedure the following compounds are prepared:

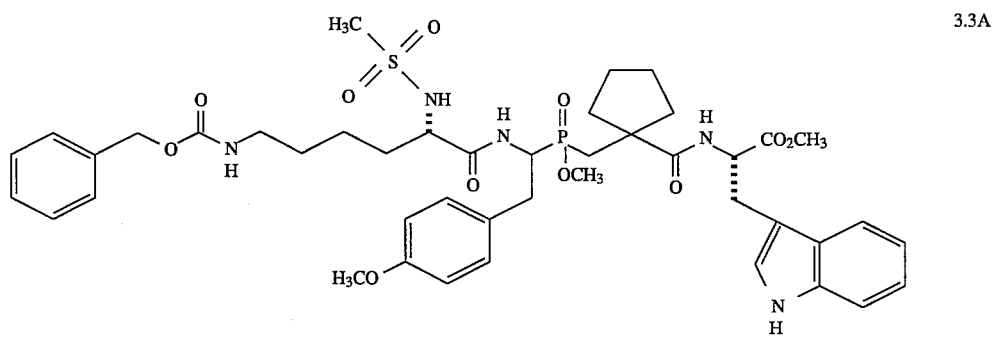

3.3A

FAB MS m/z 896 (M+H)⁺.

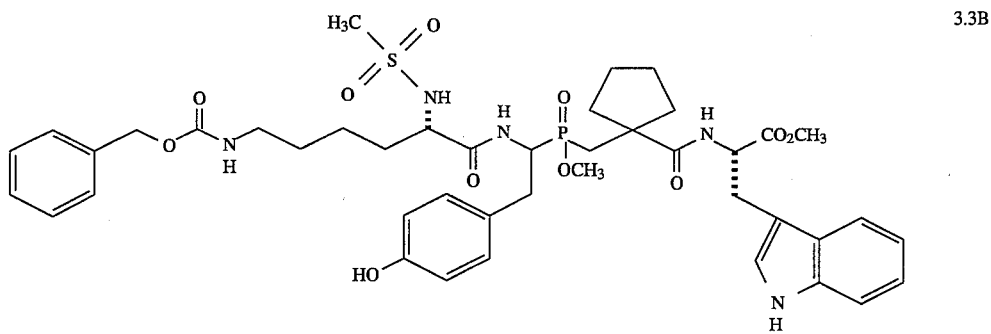

3.3B

FAB MS m/z 851.4 (M-OCH$_3$+H)$^+$.

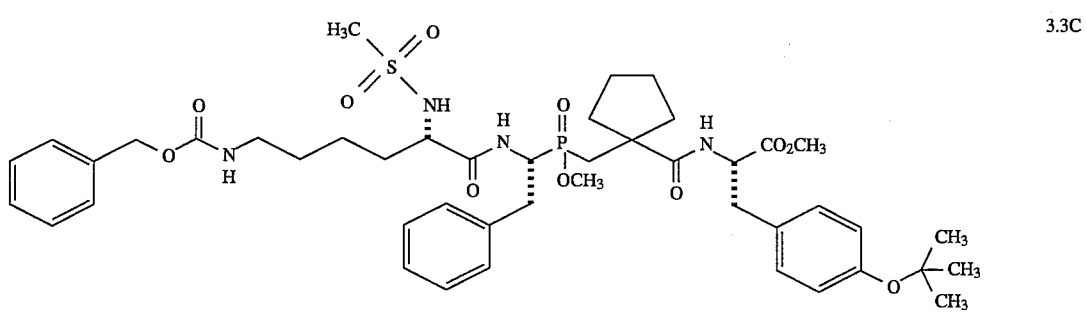

3.3C

FAB HRMS calcd for C$_{45}$H$_{64}$N$_4$O$_{11}$PS 899.4030 (M+H)$^+$. Found 899.5338.

Step 4:

Stir a solution of Example 3.3 (3.70 g, 4.27 mmol) in 96.4 CH$_2$Cl$_2$/4M HCl-dioxane (400 ml) at R.T. overnight. Concentrate the reaction mixture in vacuo to obtain the methyl ester of compound 3 as a foam. FAB MS m/z 852.1 (M+H)$^+$. Treat with LiOH.H$_2$O, acidify and extract in a manner similar to that described in Example 2 to obtain the title compound, 3, (3.10 g, 87%) as a white solid. Anal. calcd for C$_{41}$H$_{52}$N$_5$O$_{10}$PS.1.1H$_2$O: C, 57.41; H, 6.37; N, 8.17; P, 3.61%. Found: C, 57.06; H, 5.99; N, 8.03; P, 4.01%. FAB MS m/z 838 (M+H)$^+$.

Using appropriate starting materials and essentially the same procedure the following compounds are prepared:

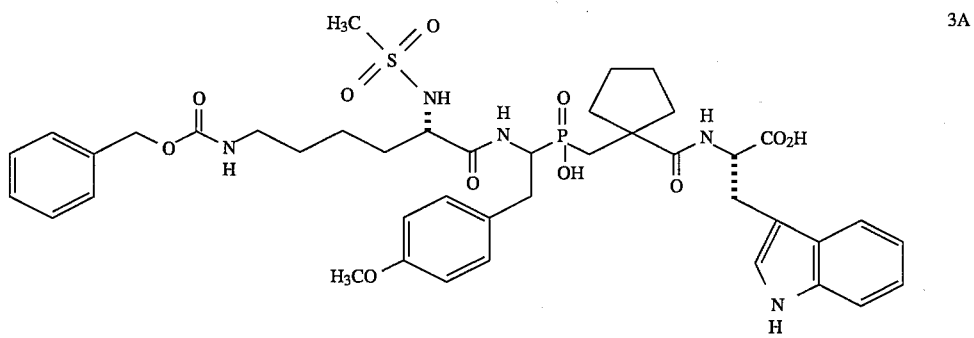

3A

FAB HRMS calcd for C$_{42}$H$_{55}$N$_5$O$_{11}$PS 868.3356 (M+H)$^+$. Found 868.3405

Anal. calcd for $C_{41}H_{52}N_5O_{11}PS \cdot 1.5H_2O$: C, 55.90; H, 6.29; N, 7.95; P, 3.52%. Found: C, 56.03; H, 5.95; N, 7.79; P, 3.48%. FAB MS m/z 854.5 $(M+H)^+$.

Using a procedure similar to that described in Example 3, Steps 1–4, the following compounds are prepared:

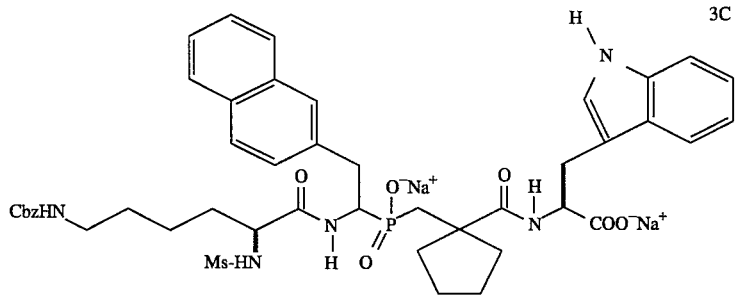

3C

HRMS (FAB): Calcd for $C_{45}H_{52}N_5O_{10}PSN_{a3}$, m/e 954.2866; measured 954.2856.

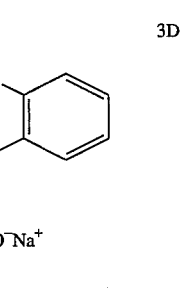

3D

HRMS (FAB): Calcd for $C_{38}H_{54}N_5O_{10}Na$, m/e 826.3227; measured 826.3204.

EXAMPLE 4

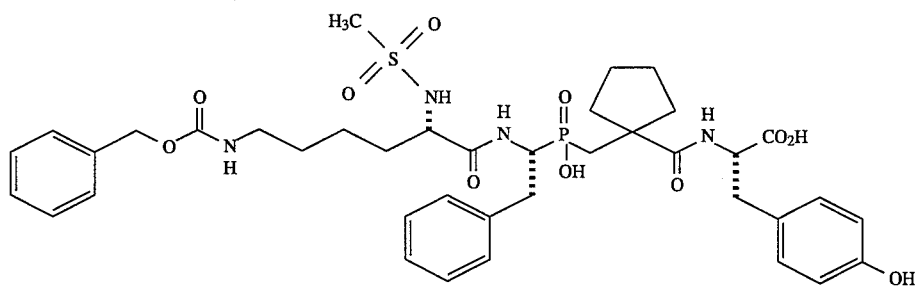

4

To a stirred solution of compound 3.3C (276 mg, 0.31 mmol) in $CH_2Cl_2$ (4 ml), add $CF_3CO_2H$ (8 ml). After 4 h, evaporate the reaction mixture to dryness. Take up the residue in $CH_3OH$, filter and evaporate to dryness. Disslove the resultant foam in $CH_3OH$ (2 ml), and add $LiOH \cdot H_2O$ (63 mg, 1.5 mmol) and $H_2O$ (2 ml) and stir overnight. Acidify the aq. solution to pH 1 with 1M HCl, collect the precipitate, wash with $H_2O$, air-dry and dry in vacuo. Column chromatography of the crude product (C18, $H_2O$ then 1:1 $H_2O/CH_3OH$) affords a mixture of the desired product and the corresponding methyl ester (142 mg), as determined by $^1H$ nmr spectroscopy. Treat the mixture with $LiOH \cdot H_2O$ (25 mg, 0.60 mmol) in 1:1 $CH_3OH/H_2O$ (6 ml) for 3 h. Evaporate the $CH_3OH$ in vacuo, acidify (pH 1) the resulting aq. solution with 1M HCl, filter the resulting precipitate, wash with $H_2O$, air-dry and dry in vacuo to give compound 4 (124 mg, 50%) as a white powder. Anal. calcd for $C_{39}H_{51}N_4O_{11}PS \cdot H_2O$: C, 56.24; H, 6.41; N, 6.73%. Found: C, 56.40; H, 6.11; N, 6.69%. FAB HRMS calcd for $C_{39}H_{52}N_4O_{11}PS$ $(M+H)^+$ 815.3091. Found 815.3107.

EXAMPLE 5

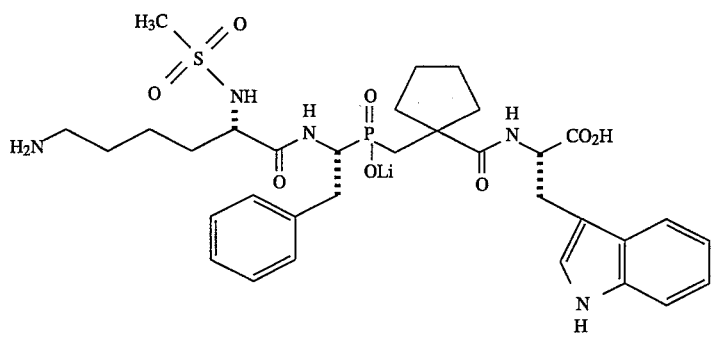

5

Stir a solution of compound 3 (106 mg, 0.127 mmol) and LiOH.H$_2$O (5.3 mg, 0.126 mmol) in 1:1 CH$_3$OH-H$_2$O (8 ml) containing 10% Pd/C (10 mg) under H$_2$ for 15 h. Remove the catalyst by filtration through celite and wash the filter pad with CH$_3$OH and H$_2$O. Concentrate the combined filtrate and washings in vacuo to remove CH$_3$OH and lyophilize the resulting aq. solution to give compound 5 (88.9 mg, 99%) as a white powder. FAB HRMS calcd for C$_{33}$H$_{46}$N$_5$O$_8$PLiS (M+H)$^+$ 710.2965. Found 710.2983. $[\alpha]_D = -18.9°$ (c 0.94 H$_2$O).

Using appropriate starting materials and essentially the same procedure the following compounds are prepared:

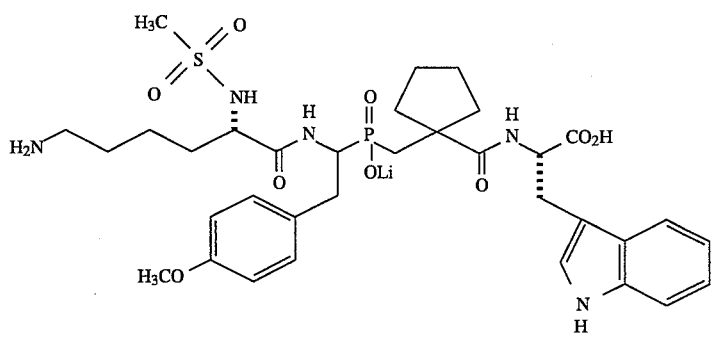

5A

FAB HRMS calcd for C$_{34}$H$_{48}$N$_5$O$_9$PLiS (M+H)$^+$ 740.3070. Found 740.3088.

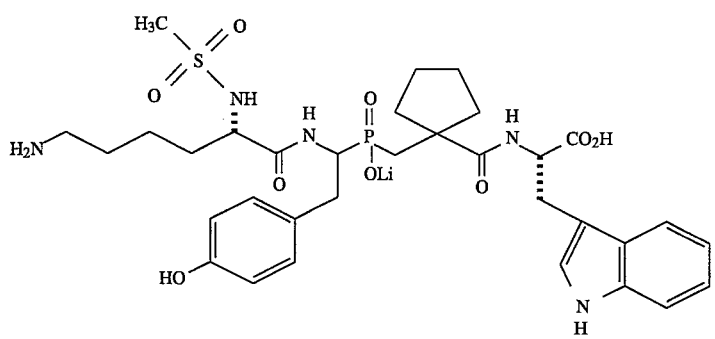

5B

FAB MS m/z 726.5 (M+H)$^+$.

FAB MS 687 (M+H)⁺.

EXAMPLE 6

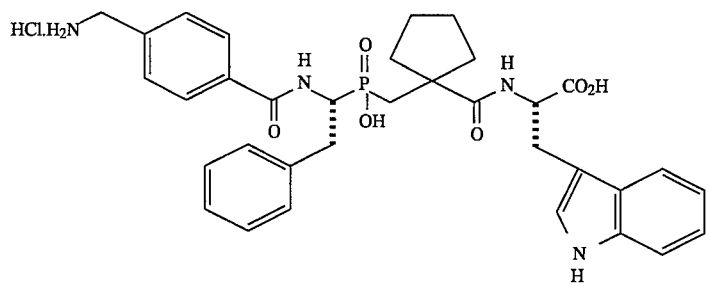

Step 1:

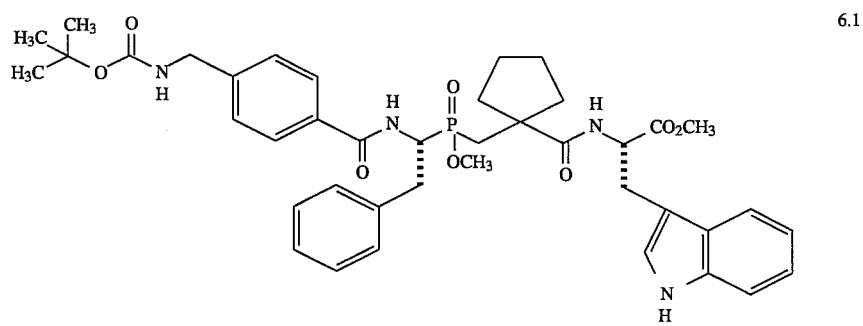

To a stirred ice-cold suspension of 4-((1,1-dimethylethoxycarbonyl)amino)methylbenzoyl chloride freshly prepared from Preparation 1 (0.60 g, 2.39 mmol), (COCl)$_2$ (0.21 ml, 2.4 mmol) and DMF (2 drops) in CH$_2$Cl$_2$ (15 ml), add a solution of compound 3.2 (1.20 g, 2.28 mmol) and N-methylmorpholine (0.53 ml, 4.8 mmol) in CH$_2$Cl$_2$ (14 ml). Stir the reaction mixture for 3 h, then wash with 1M HCl (50 ml), sat'd NaHCO$_3$ and sat'd NaCl, dry (MgSO$_4$), filter and evaporate. Flash chromatograph the residue (3% CH$_3$OH/CH$_2$Cl$_2$) to obtain compound 6.1 (1.19 g, 69%) as an off-white solid. FAB MS m/z 759 (M+H)⁺.

Using appropriate starting materials and essentially the same procedure the following compounds are prepared:

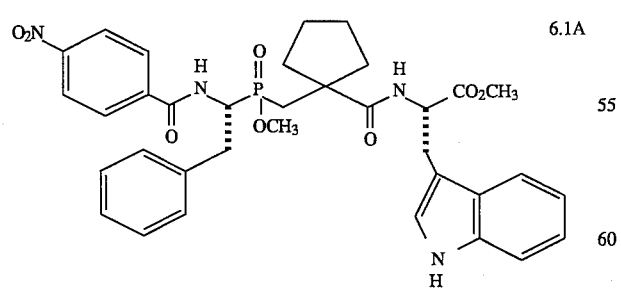

FAB HRMS calcd for C$_{35}$H$_{40}$N$_4$O$_8$P (M+H)⁺ 675.2584. Found 675.2570.

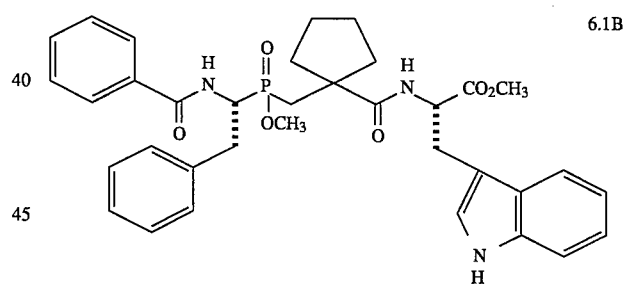

FAB MS m/z 630.4 (M+H)⁺.

Step 2:

Using the procedure of Example 3, Step 4 compounds 6.1, 6.1A and 6.1B are deprotected to obtain:

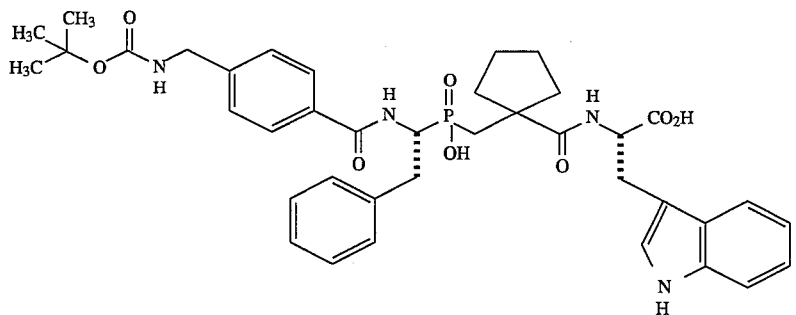

6.2

Anal. calcd for $C_{39}H_{47}N_4O_8P \cdot H_2O$: C, 62.56; H, 6.61; N, 7.48; P, 4.14%. Found: C, 62.84; H, 6.48; N, 7.67; P, 4.24%. FAB MS m/z 731.4 $(M+H)^+$.

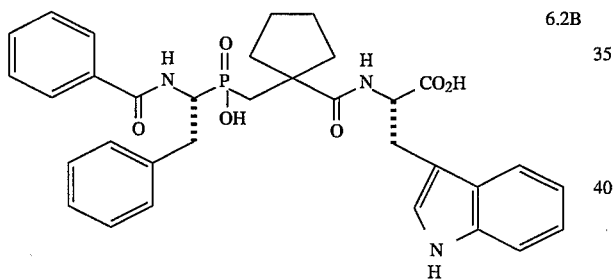

6.2A

FAB MS m/z 647.3 $(M+H)^+$.

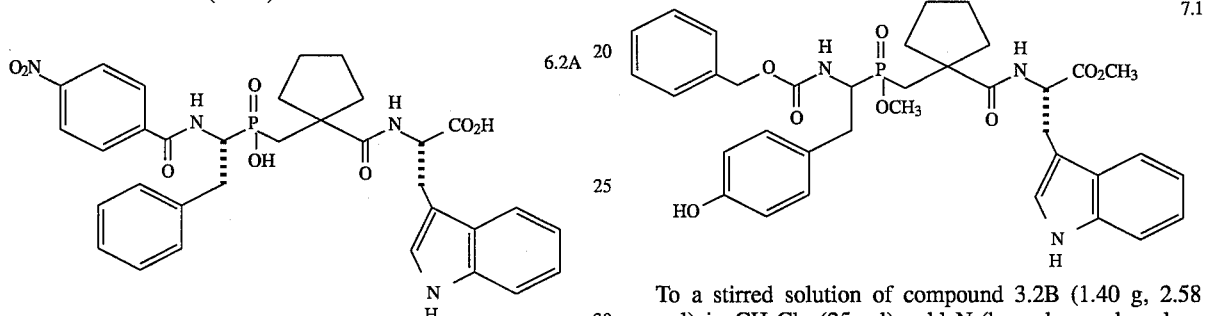

6.2B

Anal. calcd for $C_{33}H_{36}N_3O_6P \cdot H_2O$: C, 63.96; H, 6.18; N, 6.78; P, 4.93%. Found: C, 63.74; H, 5.82; N, 6.72; P, 4.99%.

Step 3:

Stir a mixture of compound 6.2 (300 mg, 0.41 mmol) and 4M HCl/dioxane (50 ml) for 2.5 h. Evaporate the reaction mixture to dryness to obtain the title compound, 6, (0.27 g, 100%) as a beige powder. FAB MS m/z 631 $(M-HCl+H)^+$.

EXAMPLE 7

Step 1:

7.1

To a stirred solution of compound 3.2B (1.40 g, 2.58 mmol) in $CH_2Cl_2$ (25 ml), add N-(benzyloxycarbonyloxy)succinimide (0.71 g, 2.85 mmol). After 30 h, dilute the reaction mixture with EtOAc (200 ml) and wash the solution with 1M HCl (200 ml), sat'd $NaHCO_3$ (200 ml) and sat'd NaCl (200 ml), then dry ($MgSO_4$), filter and evaporate. Flash chromatography (5% $CH_3OH/CH_2Cl_2$) affords compound 7.1 (1.22 g, 70%) as a white solid. FAB MS m/z 676.4 $(M+H)^+$.

Step 2:

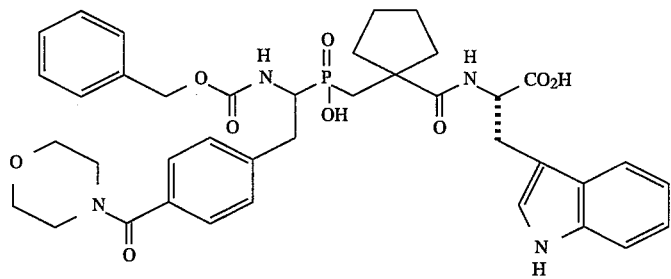

7

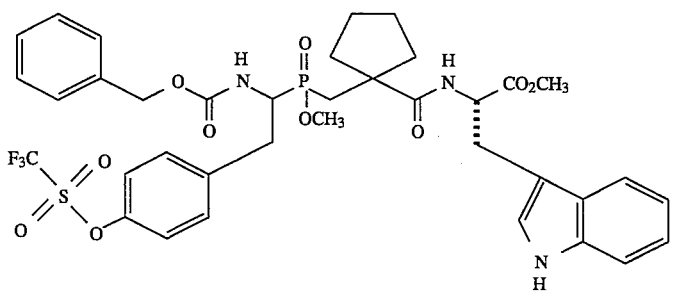

7.2

To a stirred ice-cold solution of compound 7.1 (1.090 g, 1.61 mmol) and triethylamine (0.27 ml, 1.9 mmol), add N-phenyl triflimide. Allow the reaction mixture to warm to R.T. and stir for 20 h, then partition between EtOAc (150 ml) and 1M HCl (150 ml). Wash the organic layer with sat'd NaHCO₃ (150 ml) and sat'd NaCl (150 ml), then dry (MgSO₄), filter and evaporate to dryness. Flash chromatography (20% hexanes/EtOAc then EtOAc) affords compound 7.2 (1.070 g, 82%) as a foam. Anal. calcd for $C_{37}H_{41}N_3O_{10}PF_3S \cdot 0.5H_2O$: C, 54.41; H, 5.18; N, 5.14%. Found C, 54.21; H, 5.07; N, 5.05%. FAB MS m/z 808.6 $(M+H)^+$.

Step 3:

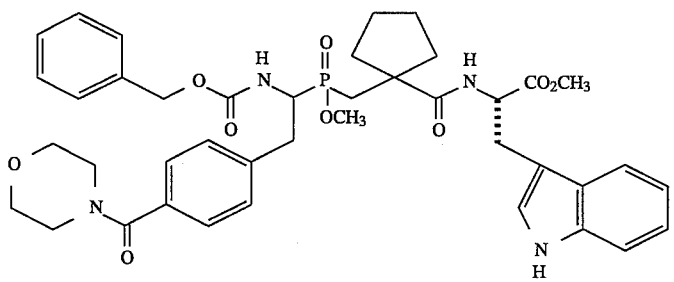

7.3

To a solution of compound 7.2 (150 mg, 0.186 mmol) and morpholine (0.50 ml, 5.7 mmol) in DMF (1 ml), add 1,3-bis(diphenylphosphino)propane (16 mg, 0.039 mmol) and Pd(OAc)2 (5 mg, 0.02 mmol), then bubble CO through the mixture for 3 min. Heat the mixture at 70° C. under a CO atmosphere for 6 h and allow to cool to R.T. Add EtOAc (15 ml) and wash the solution with 1M HCl (2×15 ml), H₂O (4×15 ml) and sat'd NaCl. Treat the organic layer with a solution of Ch₂N₂ in Et₂O until the yellow color persists, and decompose the excess Ch₂N₂ by adding CH₃CO₂H. Dry (MgSO4), filter and concentrate. Flash chromatography (4% CH₃OH/CH₂Cl₂) of the residue affords compound 7.3 (99 mg, 69%) as a colorless glass. FAB MS m/z 773.5 $(M+H)^+$.

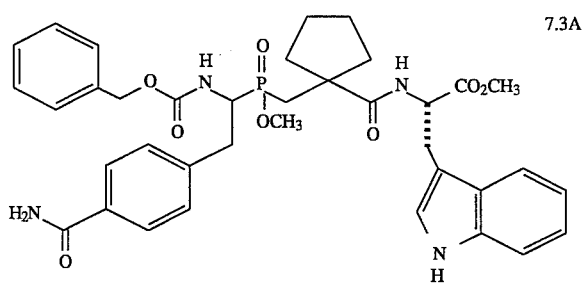

7.3A

To a solution of compound 7.2 (200 mg, 0.25 mmol) and triethylamine (77 µl, 0.55 mmol) in DMF (1 ml) add 1,3-bis(diphenylphosphino)propane (20 mg, 0.048 mmol) and Pd(OAc)2. Bubble NH₃ through the mixture for 2 min., then bubble CO through the mixture for 2 min. Place the mixture under a balloon containing a mixture of CO and NH₃ and heat to 70° C. for 6 h. Allow the reaction mixture to cool, dilute with EtOAc (15 ml), then wash with H₂O (6×5 ml) and sat'd NaCl. Dry (MgSO₄), filter and concentrate. Flash chromatography (5% MeOH/CH₂Cl₂) of the residue affords compound 7.3A (63 mg, 36%) as a colorless glass. ¹H Nmr (CD₃OD) δ7.62–7.49 (3H, m), 7.42–7.29 (2H, m), 7.20–7.01 (6H, m), 6.99–6.79 (5H, m), 4.88–4.63 (3H, m), 4.62–4.53 (1H, m), 4.13–3.92 (1H, m), 3.50–3.32 (6H, m), 3.19–2.38 (4H, m), 2.20–1.72 (4H, m), 1.55–1.22 (6H, m).

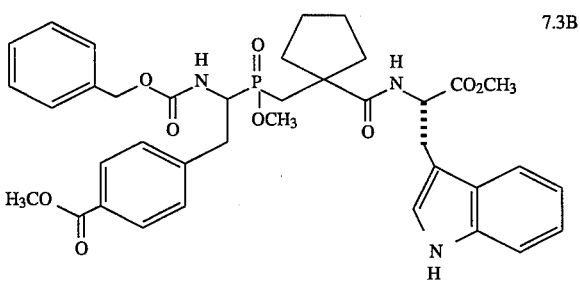

7.3B

Use a procedure similar to that described above, but omit NH₃ and include CH₃OH in the reaction mixture to obtain compound 7.3B. FAB MS m/z 718.5 $(M+H)^+$.

Step 4:

Sequentially deprotect compound 7.3 (93 mg, 0.12 mmol) with HCl/1,4-dioxane/CH₂Cl₂ and LiOH·H₂O as described in Example 3, Step 4 to afford the title compound (75 mg, 83%) as an off-white powder. Anal. calcd for $C_{39}H_{45}N_4O_9P \cdot 2.5H_2O$: C, 59.31; H, 6.38; N, 7.09; P, 3.92%. Found C, 59.12; H, 6.03; N, 7.02; P, 4.37%. FAB MS m/z 745.5 $(M+H)^+$.

EXAMPLE 8

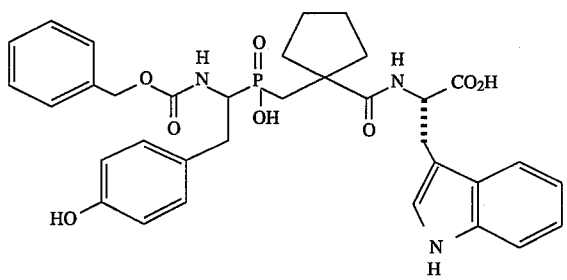

Sequentially deprotect compound 7.1 (46 mg, 0.068 mmol) with HCl/1,4-dioxane/CH$_2$Cl$_2$ and LiOH.H$_2$O as described in Example 3, Step 4, to obtain compound 8 (41 mg, 92%). Anal. calcd for C$_{34}$H$_{38}$N$_3$O$_8$P.2H$_2$O: C, 59.73; H, 6.19; N, 6.15%. Found C, 59.96; H, 5.83; N, 6.14%. FAB MS m/z 648.3 (M+H)$^+$.

In a similar manner, deprotect compounds 7.3A and 7.3B to obtain the following compounds 8A and 8B, each of which are mixtures of 2 diastereomers:

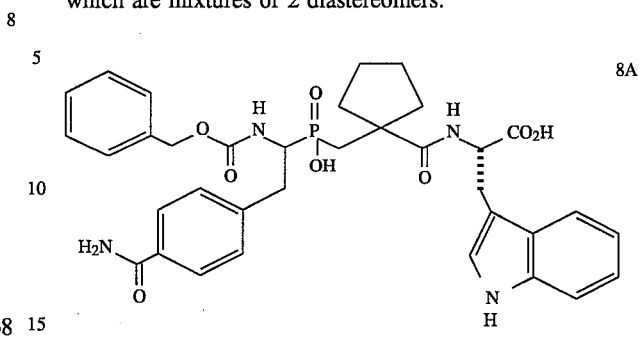

Anal. calcd for C$_{35}$H$_{39}$N$_4$O$_8$P.2H$_2$O: C, 59.15; H, 6.10; N, 7.88%. Found: C, 59.31; H, 5.74; N, 7.15%. FAB MS m/z 675 (M+H)$^+$.

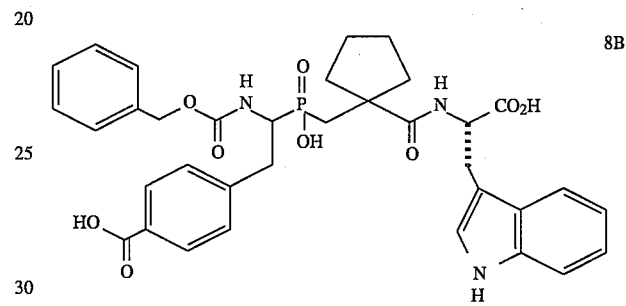

Anal. calcd for C$_{35}$H$_{38}$N$_3$O$_9$P.1.5H$_2$O C, 59.82; H, 5.88; N, 5.98; P, 4.41%. Found: C, 59.69; H, 5.64; N, 5.89; P, 4.62%.

EXAMPLE 9

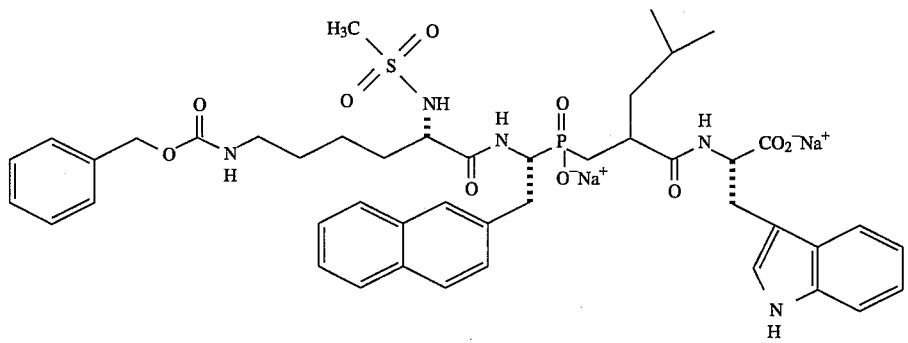

Step 1:

To a solution of 2-naphthyl triflate (90 g, 326 mmol) in DMF (240 ml), add triphenylphosphine (9.6 g, 36.6 mmol), vinyl acetate (149 g, 1862 mmol) and palladium acetate (3.8 g, 17 mmol). Reflux the reaction mixture for 1 h, then quench by addition of sat'd NaHCO$_3$ solution. Extract the mixture with Et$_2$O, dry and concentrate. Purify the residue by chromatography on silica gel (5% EtOAc in hexane) to obtain 35 g (165 mmol, 51%) 2-(2-naphthyl)vinyl acetate.

To a warm solution of aminodiphenylmethane (106 g, 578 mmol) and dry H$_3$PO$_2$ (95 g, 1376 mmol) in dioxane (200 ml), under vigorous stirring, add a solution of 2-(2-naphthyl)-vinyl acetate (70 g, 330 mmol) in dioxane (200 ml). To this mixture add conc. HCl (30 ml), reflux for 3 h, and then allow to cool to R.T. Collect the white precipitate by filtration, wash with CH₃OH and dry to obtain the hypophosphorous acid (120 g, 91% of theory). ¹H NMR (200 MHz, Acetic acid-d₄) δ3.5–3.75 (m, 1H), 3.85–4.00 (m, 1H), 4.10–4.25 (m, 1H), 5.92 (s, 1H), 6.15–9.00 (d, J=570 Hz 1H), 7.55–8.25 (m, 17H).

Step 2:

Stir a mixture of the product of Step 1 (80 g, 200 mmol), CF₃CO₂H (150 ml) and anisole (150 ml) at 85°–90° C. for 3 h. Remove the volatiles under high vacuum. Triturate the residue with CH₂Cl₂. Collect the precipitate by filtration.

Dissolve the resultant residue in 10% aq. NaOH (140 ml) and dilute to 550 ml with H₂O. Cool the solution in an ice bath and add benzylchloroformate (83.65 g, 490 mmole) dropwise, while maintaining the pH of the solution between 10–12 by addition of 10% aq. NaOH. After the addition of benzylchloroformate, acidify the reaction mixture to pH 1 using conc. HCl. Add EtOAc (500 ml) to the reaction mixture to precipitate the product and collect by filtration (55 g, 75%).

To a solution of the resultant residue (7.5 g, 20.3 mmol) in a mixture of dioxane (300 ml) and CH₃OH (40 ml) cooled to 0° C., add a solution of trimethylsilyldiazomethane in hexane (Aldrich) dropwise until a yellow color persists. Stir the reaction mixture at 0° C. for 30 min and concentrate in vacuo. Purify the product by chromatography on silica gel, eluting with 3% CH₃OH in CH₂Cl₂ to obtain 7.2 g of product (93%). MS (FAB) m/e 384 (M+H)⁺.

Step 3:

To a solution of the product of Step 2 (7.2 g, 18.8 mmol) and Preparation 11 (8.5 g, 30.5 mmol) in deoxygenated, dry THF (100 ml) cooled to −78° C. under argon, add a dispersion of NaH in oil (70 mg, 60%, 1.8 mmol). Discontinue cooling and allow the reaction mixture to warm to R.T. After 1 h, quench the reaction by addition of sat'd. aq. NH₄Cl (200 ml). Extract the organic phase with Et₂O (3×200 ml) and wash with brine. Dry the combined organic phase over MgSO₄ and concentrate under vacuum. Purify the crude product by chromatography on silica gel, eluting with 30% EtOAc in hexanes to obtain 11.0 g of product (88%). ¹H NMR (300 MHz, CDCl₃) δ0.85–1.00 (m, 6H), 1.27–1.40 (m, 1H), 1.45–1.70 (m, 2H), 1.80–2.00 (m, 1H), 2.27–2.40 (m, 1H), 2.90–3.55 (m, 3H), 3.62–3.76 (m, 3H), 4.87–4.95 (m, 6H), 4.5 (m, 1H), 4.90–5.23 (m, 5H), 6.85–7.90 (m, 15H).

Step 4:

Mix the product of Step 3 (11.0 g, 16.6 mmol) with a solution of CF₃CO₂H (50 ml) in anisole (20 ml) and cool to 0° C. Stir the reaction mixture for 40 min and remove the volatiles under kugel rhorer distillation at R.T. Dissolve the resultant residue in DMF (100 ml) and add tryptophan methyl ester hydrochloride (8.45 g, 33.17 mmol), HOBT (3.9 g, 29 mmol), EDCI (14.5 g, 48.8 mmol) and N-methylmorpholine (15.6 g, 154 mmol). Stir the reaction mixture at R.T. for 18 hrs under argon. Add dilute HCl (1N, 200 ml), then extract with Et₂O (3×150 ml). Wash the combined organic layer with brine and sat'd NaHCO₃ solution. Purify the crude product by chromatography on silica gel (5% CH₃OH in EtOAc) to obtain 9.5 g (71%) of the desired product. ¹H NMR (300 MHz, CDCl₃) δ0.70–1.50 (m, 6H), 1.05–2.10 (m, 4H), 2.20–2.40 (m, 1H), 2.70–3.50 (m, 5H), 3.55–3.90 (m, 6H), 4.35–4.55 (m, 1H), 7.00–8.60 (m, 17H). MS (FAB) m/e calcd for 712.3164, found 712.3152 (M+H)⁺.

Step 5:

To a solution of the product of Step 4 (300 mg, 0.42 mmol) in ethyl alcohol (100 ml), add palladium on carbon (10%, 100 mg). Hydrogenate the suspension at 60 psi for 2 hrs. Remove the catalyst by filtration and concentrate the filtrate in vacuo.

Using a procedure similar to that described in Step 4, couple the resultant amine (780 mg, 1.31 mmol) with ε-CBZ-α-Ms-Lys (1.00 g, 2.8 mmol) to obtain 660 mg (72% theory) of the product as a mixture of two sets of diastereomers in 1:2 ratio. Less polar diastereomer: ¹H NMR (300 MHz, CD₃OD) d 0.95 (d, J=7.0 Hz, 3H), 1.03 (d, J=7.0 Hz, 3H), 1.20–1.75 (m, 9H), 1.83 (s, 3H), 1.87–2.02 (m, 1H), 2.13–2.30 (m, 1H), 2.80–3.10 (m, 5H), 3.15–3.80 (m, 8H), 4.65–4.80 (m, 2H), 5.11 (s, 2H), 7.0–7.9 (m, 17H). MS (FAB) m/e 918.8 (M+H)⁺. More polar distereomer: ¹H NMR (300 MHz, CD₃OD) d 0.7–1.1 (m, 12H), 1.2–145 (m, 2H), 1.55–1.77 (m, 1H), 1.80–2.05 (m, 1H), 2.10–2.32 (m, 1H), 2.40–3.50 (m, 9H), 3.55–3.85 (m, 7H), 4.70–4.90 (m, 2H), 5.10–5.15 (m, 2H), 7.0–7.9 (m, 17H). MS (FAB) m/e 918.8 (M+H)⁺.

Step 6:

To a solution of 2.7 g of the product of Step 6 in THF (100 ml), add 0.5 m aq NaOH (100 ml). Stir the reaction mixture at R.T. for 15 h and adjust the pH to 8 by addition of dilute HCl. Remove the solvents under high vacuum and subject the residue to reverse phase HPLC (C-18 column, elution with CH₃OH/H₂O) to obtain three diastereomers: A (400 mg, 14.5% theory); B (720 mg, 26% theory); and C (350 mg, 12.7% theory).

A: ¹H NMR (400 MHz, CD₃OD) δ0.95 (d. J=6.5 Hz, 6H) 1.78 (s, 3H), 1.15–1.80 (m, 11H) 2.87–3.02 (m, 4H), 3. 22 (m, 1H), 3.53 (d, J=12 Hz, 1H), 3.70 (m, 1H), 4.45 (m, 1H), 4.63 (m, 1H), 5.10 (s, 2H), 6.90–7.87 (m, 17H). MS (FAB) m/e calcd for 956.3016, found 956.3022 (M+Na)⁺.

B: ¹H NMR (400 MHz, CD₃OD) δ0.63 (d, J=6.5 Hz, 3H), 0.86 (d, J=6.5 Hz, 1.5H), 0.94 (d, J=6.5 Hz, 1.5H), 0.90–2.05 (m, 14H), 2.78 (s, 1.5H), 2.65–2.95 (m, 3H), 3.02 (m, 1H), 3.25 (m, 1H), 3.37–3.52 (m, 2H), 3.7 (m, 1H), 4.30–4.47 (m, 1H), 4.63 (m, 0.5H), 4.79 (m, 0.5H), 5.07–5.15 (m, 2H), 6.98–7.85 (m, 17H). MS (FAB) m/e 912 (M+2H−Na)⁺ 912.

C: ¹H NMR (400 MHz, CDCl₃) δ0.70 (m, 6H), 0.80–1.18, m, 7H), 1.50 (m, 2H), 1.67 (m, 1H), 1.88 (m, 1H), 2.67–2.87 (m, 3H), 2.90 (s, 3H), 2.97 (m, 1H), 3.22 (m, 1H), 3.51 (m, 2H), 3.79 (m, 1H),4.47 (m, 1H), 4.82 (m 1H),5.15 (s, 2H), 7.07 (m, 1H), 7.14 (m 1H), 7.22 (s 1H) 7.33–7.52 (m, 9H), 7.68–7.90 (m, 5H).

EXAMPLE 10

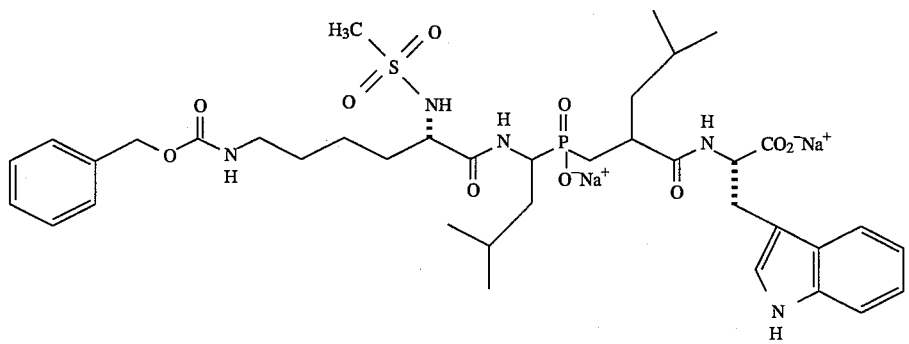

Step 1:

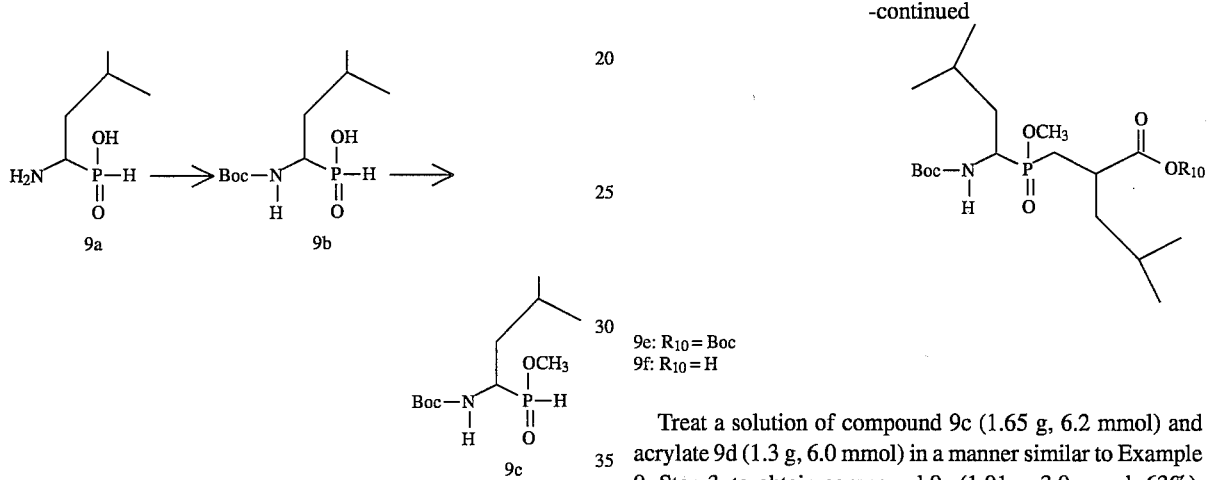

To a solution of compound 9a (4.80 g, 31 mmol) in aq. NaOH (22 ml, 1M) at R.T., add di-tert-butylcarbonate (11 g, 40 mmol) and stir at R.T. for 1 h, keeping the pH at 8–9. Extract the reaction mixture with Et$_2$O. Acidify the aqueous phase to pH 2 using 6N HCl and extract with EtOAc. Dry the organic layer and concentrate in vacuo to yield compound 9b (6.0 g, 86%). $^1$H NMR (acetone-d$_6$, 300 MHz) δ7.85 (s, 0.5H), 5.80 (s, 0.50H), 6.25 (s, 1H), 3.80 (s, 1H), 1.10–1.90 (m, 12H), 0.85 (m, 6H).

To a solution of phosphinic acid 9b (6.0 g, 27 mmol) in dioxane (20 ml) and CH$_3$OH (1 ml), add a solution of trimethylsilyldiazomethane in hexane (Aldrich) until a yellow color persists. Stir the reaction mixture at R.T. overnight. Remove solvents in vacuo and the chromatograph the residue on silica gel, eluting with 2% CH$_3$OH in CH$_2$Cl$_2$ to afford compound 9c (4.4 g, 61%). $^1$H NMR (CDCl$_3$, 300 MHz) δ8.90 (s, 0.5H), 6.10 (s, 0.5H), 4.55–4.70 (m, 1H), 3.95–4.20 (m, 1H), 3.85 (m, 3H), 1.45 (s, 9H) 1.40–1.90 (m, 3H), 0.95–1.05 (m, 6H).

Step 2:

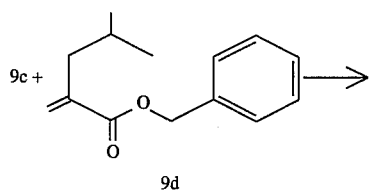

9e: R$_{10}$ = Boc
9f: R$_{10}$ = H

Treat a solution of compound 9c (1.65 g, 6.2 mmol) and acrylate 9d (1.3 g, 6.0 mmol) in a manner similar to Example 9, Step 3, to obtain compound 9e (1.91 g, 3.9 mmol, 63%). $^1$H NMR (CDCl$_3$) δ7.30–7.42 (m, 5H), 5.12 (m, 2H), 3.45–3.80 (m, 3H), 2.80–3.15 (m, 1H), 1.40 (br. s, 9H), 1.10–2.20 (m, 9H), 0.80–1.00 (m, 12H).

To a solution of compound 9e (1.9 g, 3.9 mmol) in EtOAc (20 ml), add Pd-C (10%, 300 mg). Hydrogenate the suspension at R.T. under 60 psi for 2 h. Filter the mixture through a celite pad and concentrate the filtrate in vacuo to afford carboxylic acid 9f (1.4 g, 92%). $^1$H NMR (acetone-d$_6$, 300 MHz) δ6.00–6.30 (m, 1H), 3.80–4.10 (m, 1H), 3.55–3.65 (m, 3H), 2.70–2.90 (m, 1H), 1.30–140 (br. s, 9H), 1.30–2.20 (m, 9H). 0.75–0.95 (m, 12H).

Step 3:

Couple 9f (0.60 g, 1.5 mmol) and tryptophan methyl ester hydrochloride (48 g, 1.9 mmol) in a manner similar to Example 9, Step 4, eluting the column with 5% EtOAc in hexanes to obtain 0.540 g (63%) of desired product. $^1$H NMR (acetone-d$_6$, 300 MHz) δ6.90–7.65 (m, 6H), 5.95–6.20 (m, 1H), 4.65–4.75 (m, 1H), 3.75–4.05 (m, 1H), 3.35–3.65 (m, 6H), 3.05–3.30 (m, 2H), 2.70–2.90 (m, 1H), 1.10–2.20 (m, 9H), 1.30–1.40 (br, s, 9H), 0.65–0.95 (m, 12H).

To a solution of the resultant compound (0.40 g, 0.71 mmol) in CH$_2$Cl$_2$, stirred under argon, add CF$_3$CO$_2$H. Stir the reaction mixture at R.T. for 1 h, remove solvents in vacuo, dissolve the residue in CH$_2$Cl$_2$ and wash with aq. NaHCO$_3$. Remove solvents to obtain the desired crude amine (0.250 g, 76%).

Step 4:

Couple the product of Step 3 (0.100 g, 0.21 mmol) and ε-CBZ-α-Ms-Lys (119 g. 0.33 mmol) using the procedure of Example 9, Step 4, eluting the column with 2% CH₃OH in CH₂Cl₂ to obtain 0.110 g (61%) of product. ¹H NMR (CD₃OD): δ7.50–7.60 (m, 1H), 7.20–7.40 (m, 6H), 6.95–7.20 (m, 3H), 5.00–5.15 (br. s, 2H), 4.60–4.80 (m, 1H), 4.25–4.45 (m, 1H), 3.85–3.95 (m, 1H), 3.45–3.80 (m, 6H), 3.05–3.45 (m, 5H), 2.70–3.00 (m, 6H), 1.10–2.20 (m, 11H), 0.60–1.10 (m, 12H).

Step 5:

Dissolve the ester from Step 4 in THF (30 ml) and add a solution of NaOH (0.5N, 30 ml). Stir the reaction mixture at R.T. overnight. Remove the solvents in vacuo and subject the residue to reverse phase column chromatography on silica gel (C-18), eluting-with CH₃OH—H₂O (75% CH₃OH to 100% CH₃OH) to obtain the title compound as two fractions: 10A (0.045 g, 25%), a single diastereomer: ¹H NMR (CD₃OD): δ7.40–7.60 (m, 2H), 6.90–7.40 (m, 10H), 5.50 (s, 0.5H), 5.00–5.05 (br. s, 1.5H), 4.50–4.60 (m, 2H), 4.25–4.35 (m, 1H), 4.05–4.15 (m, 1H), 3.85–3.95 (m, 1H), 3.65–3.75 (m, 1H), 2.90 (s, 2H), 2.92–3.20 (m, 4H), 2.50–2.95 (m, 5H), 1.00–1.90 (m, 15H). 0.75–1.00 (m, 8H). MS (FAB) 850.5 (M+H)⁺, 872.5 (M+Na)⁺ 10B (0.120 g, 65%), a mixture of three diastereomers. ¹H NMR (CD₃OD): δ7.40–7.70 (m, 2H), 6.90–7.40 (m, 10H), 5.01–5.10 (br. s, 2H), 4.50–4.70 (m, 2H), 3.80–4.50 (m, 2H), 3.30–3.45 (m, 2H), 3.05–3.20 (m, 3H), 2.95 (s, 1H), 2.90 (s, 2H), 2.55–2.75 (m, 2H), 1.10–1.90 (m, 14H), 0.70–1.00 (m, 9H), 0.55–0.60 (m, 3H). MS (FAB) 850.5 (M+H)⁺, 872.5 (M+Na)⁺.

Using appropriate starting materials and following a similar procedure to that outlined in Steps 2–5 of Example 10, the following compound can also be prepared as a mixture of 4 diastereomers:

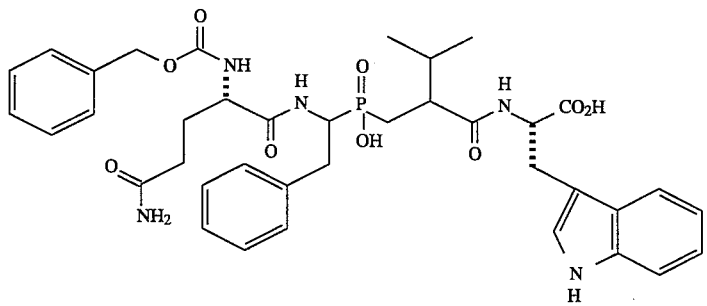

FAB MS m/z 748.3 (M+H)⁺.

Using a procedure similar to that described in Example 10, the following compounds are prepared:

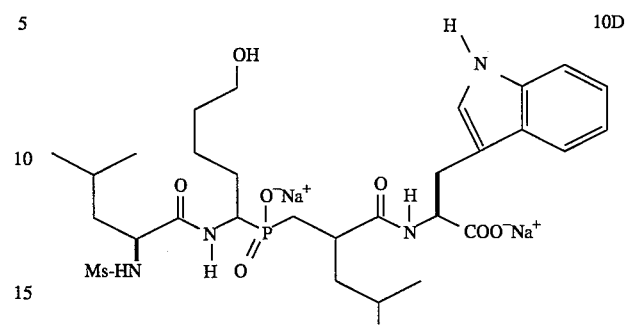

MS (FAB) m/e 739 ((M+Na)⁺, monosodium salt). ¹H NMR (400 MHz, CD₃OD) δ0.57–0.70, 0.97–1.07 (12H, m, CH₃), 0.80–1.80 (10.5H, m), 1.80–2.10 (3.5H, m), 2.55–2.75 (1H, m), 2.92 (1.8H, s), 3.01 (1.2H, s), 3.13–3.25 (1 H, m), 3.35–3.50 (1 H, m), 3.50–3.70 (2H, m), 3.85–4.10 (2H, m), 3.65 (1H, m), 6.97–7.40 (4H, m), 7.65–7.72 (1H, m).

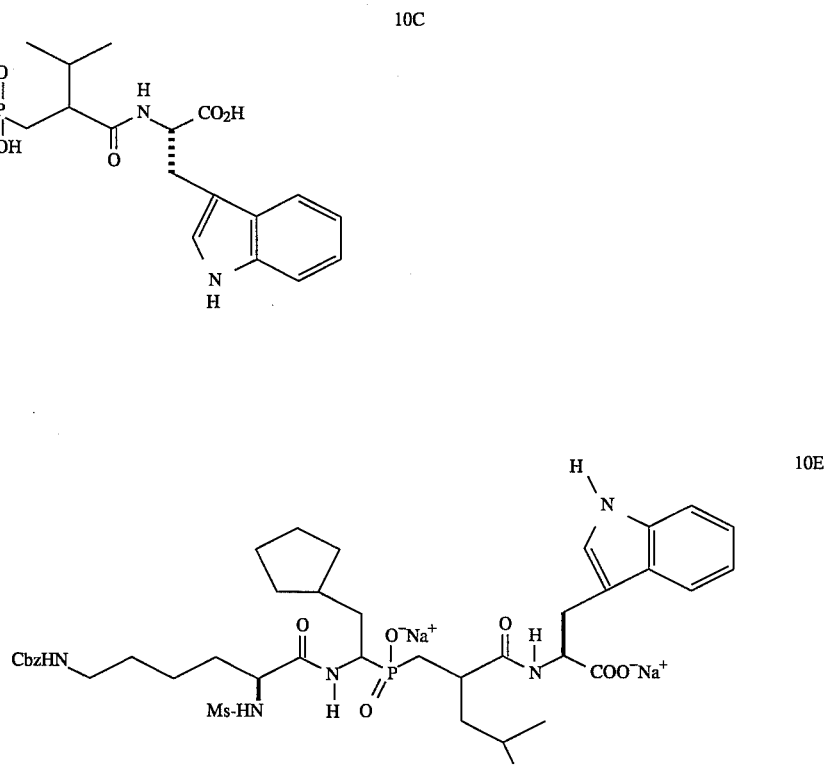

MS (FAB) m/e 854 ((M+2 Na)$^+$, disodium salt. $^1$NMR (400 MHz, CD$_3$OD) δ0.86 (3H, d, J=7.0 Hz), 0.95 (3H, d, J=7.0 Hz), 1.10–2.00 (16H, m), 2.89 (1H, m), 2.93 (3H, s), 3.02–3.22 (4H, m), 3.96 (1H, m), 4.08 (1H, m), 4.59 (1H, m), 5.08 (2H, s), 7.00–7.43 (9H, m), 7.70 (1H, d, J=8.0 Hz).

The following formulations exemplify some of the dosage forms of this invention. In each, the term "active compound" designates a compound of formula I or II.

EXAMPLE A
Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B
Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Example C
Parenteral Preparation

| Ingredient | mg/vial | mg/vial |
|---|---|---|
| Active Compound Sterile Powder | 100 | 500 |

Method of Manufacture

For reconstitution, add sterile water for injection or bacteriostatic water for injection.

The in vitro and in vivo ECE inhibitory activity of the compounds of formulae I and II can be determined by the following procedures.

BET Challenge Method:

ECE in vivo activity is determined as described by Vemulapalli et al.,in Life Sciences, 53 (1993), pp. 783–793. Briefly, male Charles River CD rats (Wilmington, Mass.) weighing 250–275 g are anesthetized with Inactin, 100 mg/kg, ip. The trachea is catheterized. The right carotid artery and the right jugular vein are cannulated to record blood pressure (BP) and to infuse drugs, respectively. The BP is recorded by connecting the arterial catheter to Statham pressure transducers and displayed on a Grass polygraph. The rectal temperature is kept at 37° C. After an equilibration period of 15–30 min, the rats are infused with saline vehicle (20 μl/min) or test compounds (0.01–0.25 mg/kg/min) throughout the study. Thirty minutes after the start of infusion, the rats are challenged with BET-1 (5 μg/kg) via the venous catheter, and the BP is monitored for another 15 min.

Figure 2:
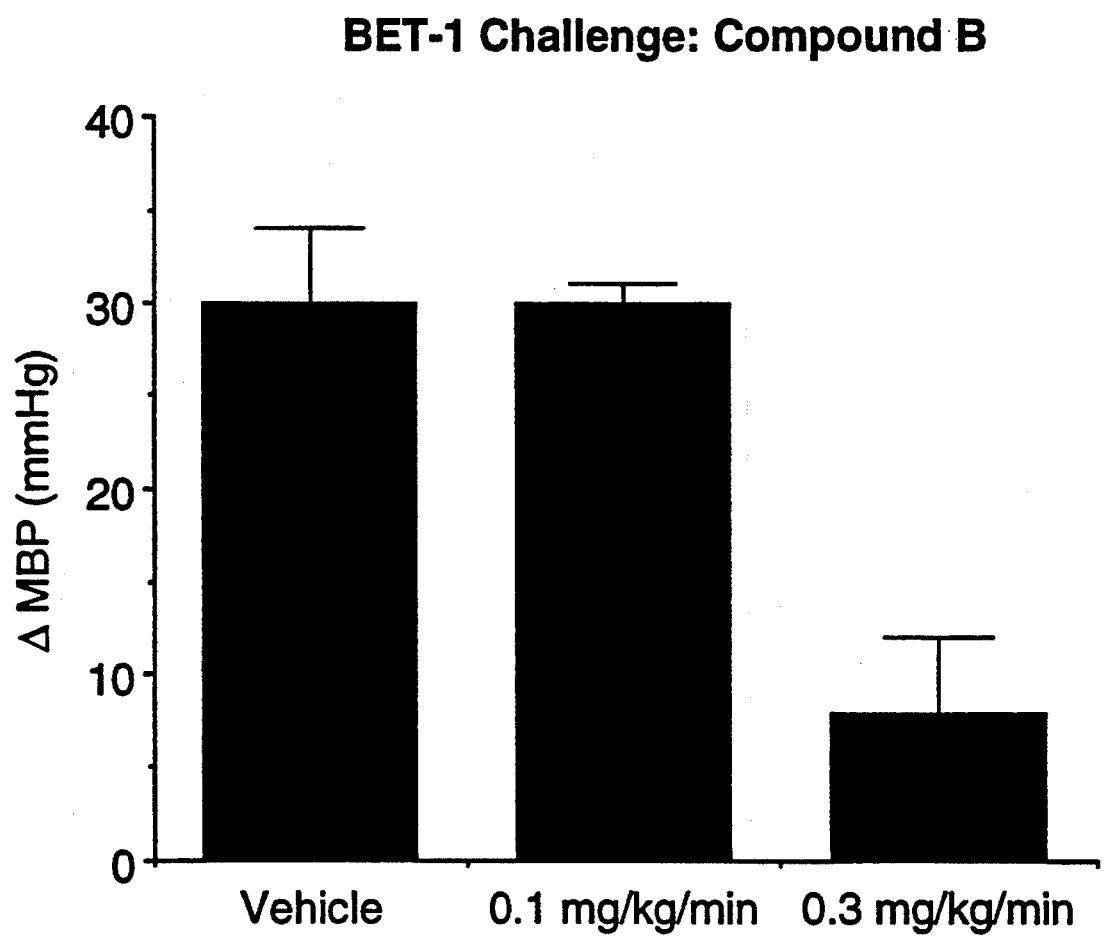

FIGS. 1 and 2 show the results of the BET challenge for two compounds of the invention:

Compound A: N-[[1-[[hydroxy-[1(R)-[[6-amino-2(S)-[(methylsulfonyl)amino]-1-oxohexyl]-amino]-2-phenylethyl]phosphinyl]methyl]cyclopentyl]carbonyl]-L-tryptophan lithium salt;

Compound B: N-[2-[[hydroxy[1-[[2(S)-[(methylsulfonyl)amino]- 1-oxo-6-[[phenylmethoxy)-carbonyl]amino] hexyl]amino]-2-(2-naphthalenyl)ethyl]phosphinyl]methyl]-4-methyl-1-oxopentyl]-L-tryptophan disodium salt.

FIG. 1 shows that compared to the vehicle, Compound A, administered at a dose of 0.1 mg/kg/min, shows an approximate 15 mmHg lower blood pressure in response to the BET-1 challenge. FIG. 2 shows that compared to the vehicle, Compound B administered at a dose of 0.1 mg/kg/min does not have an effect, while administration of a dose of 0.3 mg/kg/min shows an approximate 22 mmHg lower blood pressure in response to the BET-1 challenge.

Isolated Perfused Guinea Pig Lung Method:

The method is as described by Vemulapalli et al., in J. PharmacoL Exp. Therap., 262, 3 (1992), pp. 1062–1069. Briefly, male Dunkin-Hartley guinea pigs (400–600 g) are anesthetized with pentobarbital 30 mg/kg, ip. The trachea is cannulated to facilitate respiration. The right jugular vein is cannulated to administer saline vehicle or test compound, or compounds are administered orally or subcutaneously. Ten minutes after the administration of saline vehicle or test compound, a thoracotomy is performed and the trachea, lungs and heart are removed intact and placed in warmed Tyrode's buffer (34°–35° C.) of the following composition in mM: NaCl 120, KCl 4.8, MgSO$_4$.7H$_2$O 1.2, KH$_2$PO$_4$ 1.2, NaHCO$_3$ 25, CaCl$_2$.2H$_2$O 11.25, glucose 11 and BSA 0.5%. The pulmonary artery and trachea are cannulated and the lungs are mounted on a perfusion apparatus. Lungs are perfused at a rate of 3.2 ml/min via the pulmonary artery with oxygenated (95% O$_2$ and 5% CO$_2$) Tyrode's solution maintained at 34°–35° C. The lungs are mechanically ventilated with room air with a volume of 2.5 ml/stroke and 50 strokes/min. Pulmonary insufflation pressure (PIP) is monitored through a side arm of the perfusion apparatus with a Statham pressure transducer and recorded on a Grass polygraph. Lungs are allowed to stabilize for 15 min. Lung effluents (50 ml) are collected every 15 min into chilled polypropylene centrifuge tubes (Corning) containing 100 μl each of aprotinin (200 kallikrein inhibitory units/ml) and soybean trypsin inhibitor (20N-α-benzoyl-L-arginine ethyl ester units/ml). Ischemia-hypoxia (I/H) is produced by cessation of ventilation and perfusion for 15 min followed by reperfusion and reventilation for 60 min. At the end of the experiment, the lungs are tested for cardiopulmonary reactivity by challenging with 5-hydroxy-tryptamine (0.5 mg) directly into the lungs via a pulmonary artery cannula.

In a separate study, anesthetized guinea pigs are administered saline vehicle or test compound. Ten minutes later, the lungs are removed and mounted on a perfusion apparatus as described above. After an equilibration period of 15 min, BET-1 (30 µg over 15 min) or ET-1 (0.6 µg over 15 min) is infused directly into the perfusion medium and the effects on PIP in vehicle and test compound-treated guinea pig lungs are assessed.

FIGS. 3 to 6 show the results of four compounds of the invention on I/H-induced ET-1 release in isolated perfused guinea pig lungs. The compounds include Compounds A and B, identified above, and:

Compound C: N-(2-((1-((6-amino-2-(methylsulfonyl)amino)-1-oxohexyl)amino)2-phenylethyl)hydroxyphosphinyl)methyl)-3-methyl-1-oxobutyl)-L-tryptophan; and Compound D: N-[2-[[hydroxy[2-[1-[4-methyl-1-oxo-2-[[(phenylmethoxy)carbonyl]amino]pentyl]amino]-2-phenylethyl]phosphinyl]methyl]-4-methyl-1-oxopentyl]-tryptophan.

Figure 3:
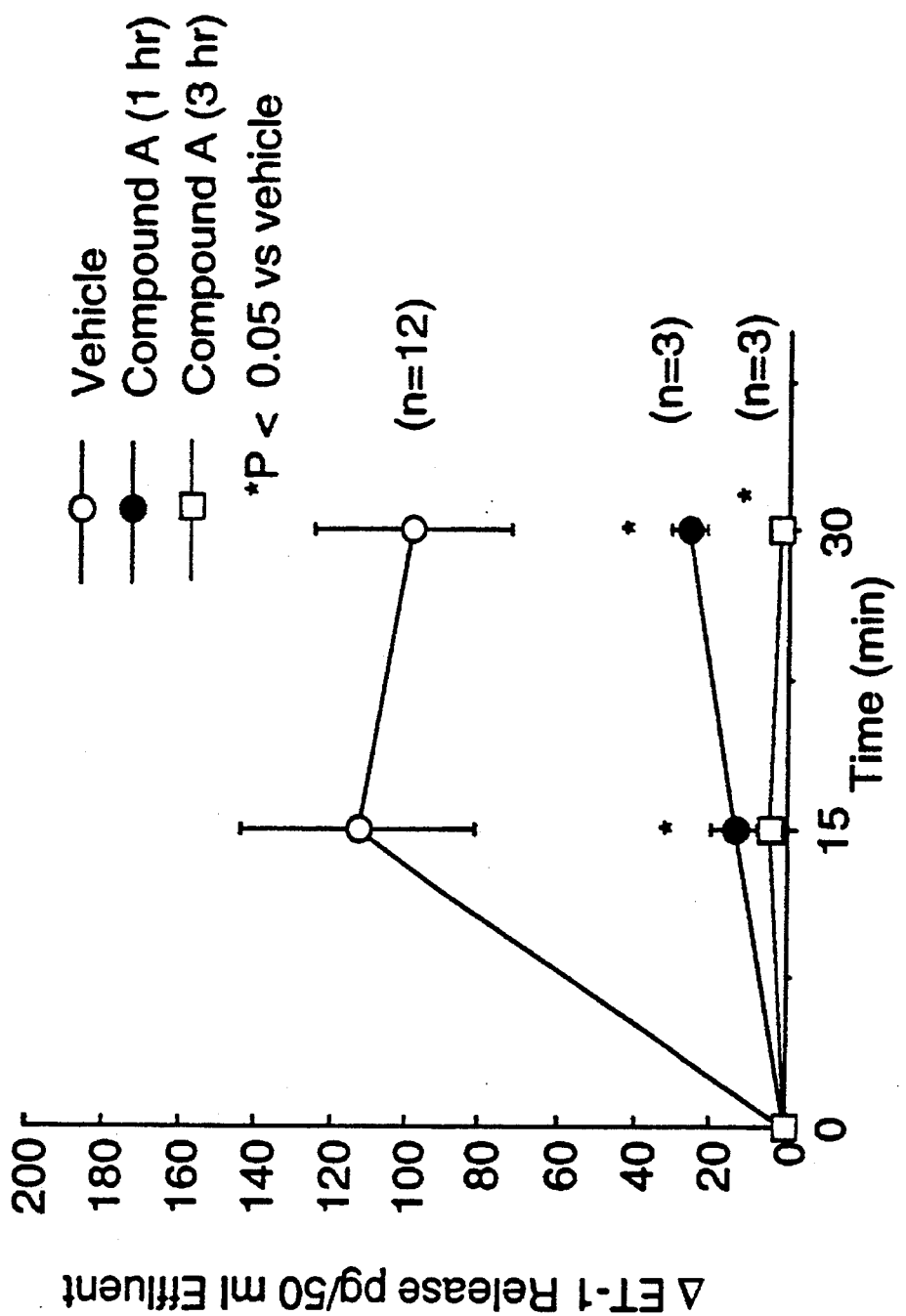

FIG. 3 shows that the elevation in PIP produced by I/H (see the results of administering vehicle only) is attenuated at 1 hour and at 3 hours by oral administration of Compound A at a dose of 30 mg/kg. The asterisks indicate statistical significance ($P<0.05$) compared to the vehicle.

Figure 4:
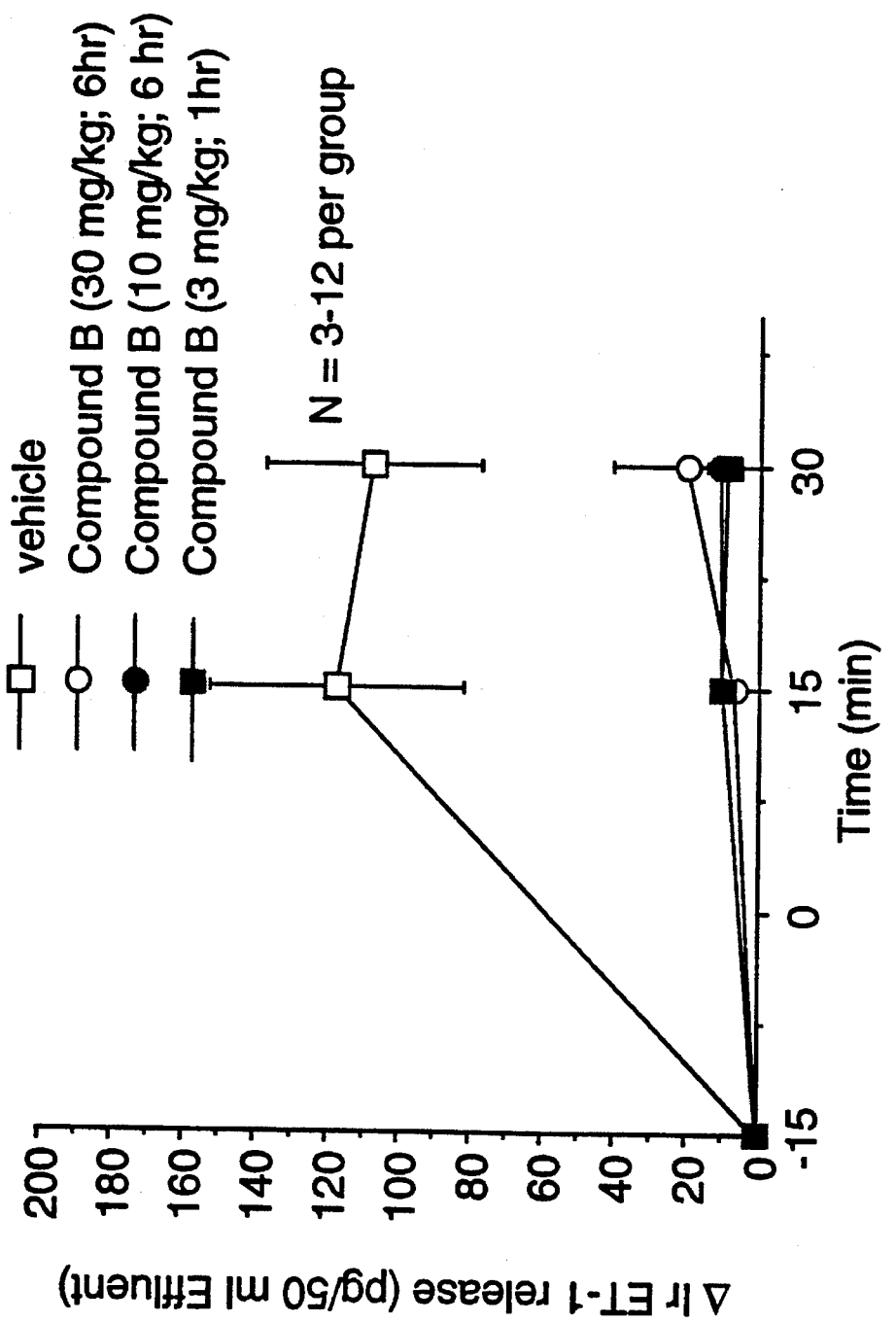

FIG. 4 shows that the elevation in PIP produced by I/H is attenuated at 1 hour by a subcutaneous (sc) administration of 3 mg/kg and at 6 hours by sc administration of 10 and 30 mg/kg of Compound B.

FIG. 5 shows that the elevation in PIP produced by I/H is attenuated by a intravenous (iv) administration of 10 mg/kg of Compound C. Similarly, FIG. 6 shows the attenuation of ET-1 release following I/H by iv administration of 10 mg/kg of Compound D.

ECE Assay Method (in vitro):

The ECE assay is based on the quantitative determination of [$^{125}$I]ET-1 released from [$^{125}$I]BET-1 labeled on Tyrosine-13 by binding to the membrane-bound ET receptor. Guinea pig lung membrane (GPLGM) was selected as a suitable tissue source of phosphoramidon-sensitive ECE. GPLGM was also found to contain a high density of ET receptors. Thus, this preparation was utilized as a source of both ECE and a saturating concentration of ET receptors for the quantitative determination of [25lI]ET-1 from the conversion of [125I ]BET-1. Under selected experimental conditions of the ECE assay, specific [125I]ET-1 bound was directly related to ECE activity. Assays were carried out in the presence of varying concentrations of test compounds to evaluate their efficacy in inhibiting ECE activity.

Preparation of Guinea Pig Lung Membrane (GPLGM):

Frozen guinea pig lungs (Keystone Biologicals,Cleveland, Ohio) are weighed and homogenized in 10 times gram tissue weight of solution A (50 mM Tris-HCl, pH 7.4, 0.25M sucrose, and 2 mM EDTA) using a Polytron tissue homogenizer (probe PTA-20S). Homogenization is repeated four times at speed setting seven each for 10 s and with 5–8 min intervals on ice in between homogenization. Homogenates are spun for 30 min at 2000 g (4100 rpm in an SS34 rotor or 3800 rpm in an SA-600 rotor). Supernatants containing membranes are carefully decanted and saved. Pellets are rehomogenized in solution A as described, and homogenates are spun at 2000 g for 30 min. Supernatants are removed, mixed with the supernatants from the first spin, and spun at 37000 rpm in a 45 Ti rotor (107022 g) for 60 min. Pellets containing membranes are suspended in solution B (10 mM Tris-HCl, pH 7.4, and 0.125M sucrose) using a Dounce homogenizer. Samples are divided into 1 ml fractions, rapidly frozen in a dry ice methanol bath, and stored at –80° C. All steps are carried out at 4° C.

Preparation of Lubro/-Treated GPLGM (L-GPLGM):

GPLGM fractions prepared as described above are thawed and resuspended at a concentration of 1 mg membrane protein/mL in a solution containing 0.06% lubrol PX, 50 mM Tris-HCl (pH 7.4), and 100 mM NaCl. Stir the mixture for 1 h and then spin for 1 h at 37000 rpm in a 45 Ti rotor (107022 g). Discard the supernatants and resuspend the pellets in a solution containing 50 mM Tris-HCl (pH 7.4), and 100 mM NaCl using a Dounce homogenizer, and adjust the final volume to half the original volume. Spin the homogenates for 1 h at 37000 rpm in a 45 Ti rotor (107022 g). Suspend the membrane pellets in solution B and treat as described above. All steps are performed at 4° C.

ECE Assay: Samples of L-GPLGM containing 20 µg protein are incubated in a solution containing 100 mM Tris-HCl (pH 7), 100 mM NaCl, and 5 mg/ml BSA (Fraction V, 98–99% albumin) (Sigma Chemical Co.) at a final reaction volume of 100 µL. The ECE assay is initiated by the addition of [$^{125}$I]BET-1 to obtain a final concentration of 500 pM. Reactions are carried out for 30 min at 37° C. Reactions are terminated by addition of 4 mL of solution C (10 mM Tris-HCl, pH 7.4, and 150 mM NaCl) at 4° C. followed by rapid filtration on Whatman GF/B glass microfiber filters. Filters are presoaked for 1 h at 4° C. in a solution containing 50 mM Tris-HCl (pH 7.4), 10 mg/mL BSA, and 0.1% sodium azide. Wash test tubes and filters four times with 4 mL of solution C at 4° C., and count radioactivity retained on the filters in a γ counter. Non-specific binding is determined in the presence of 1 µM of unlabeled ET-1 (Peninsula Laboratories, Inc., Belmont, Calif.) in the reaction mixture. All reactions are performed in duplicate.

Assay of ECE Inhibition:

To test the effect of test compounds on ECE activity, ECE assays are carried out in the presence of varying concentrations of the compounds. Assays are initiated following a 2 h incubation of L-GPLGM with the compound at 4° C. ECE activity in the presence of compounds is expressed as a percentage of control ECE activity of the membrane preparation, which is determined simultaneously. The concentration of compounds producing a 50% inhibition of ECE activity ($IC_{50}$ values) is determined from a plot of the percentage of control ECE activity versus log concentration of compounds.

Evaluation of the ECE Assays:

To evaluate the selectivity of ECE inhibition by the compounds, simultaneous experiments identical to the ECE assays are carried out using 250 pM [$^{125}$I]ET-1 instead of [$^{125}$I]BET-1. The amount of specific [$^{125}$I]ET-1 binding is expressed as a percentage of that in controls containing no compound. These results provide information about the direct effect of compounds on ET-1 binding to the receptor. Such experiments are carried out routinely throughout the investigation and results are used as an index of integrity of the ECE assay and validity of values of ECE inhibitory activity.

Protein Assay.

Protein concentrations are determined by the amido black binding assay described by Schaffner and Weissmann (1973) using BSA as a standard.

Using the in vitro ECE assay described above, ECE IC$_{50}$ (nM) data was obtained for many of the compounds shown in the examples:

| Ex. No. | IC$_{50}$ (nM) |
|---|---|
| 1 | 190 |
| 1A | 115 |
| 1B | 400 |
| 1C | 800 |
| 2 | 130 |
| 3 | 60 |
| 3A | 50 |
| 3B | 55 |
| 3C | 55 |
| 3D | 55 |
| 4 | 119 |
| 5 | 70 |
| 5A | 40 |
| 5B | 100 |
| 5C | 100 |
| 6 | 90 |
| 6.2A | 50 |
| 6.2B | 250 |
| 7 | 50 |
| 8 | 85 |
| 8A | 290 |
| 8B | 490 |
| 9A | 65 |
| 9B | 4500 |
| 9C | 4500 |
| 10A | 40 |
| 10B | 1400 |
| 10C | 200 |
| 10D | 150 |
| 10E | 55 |

Additional compounds within the scope of the present invention were prepared by methods similar to those described above and were found to have the in vitro ECE inhibition activity shown in the following table:

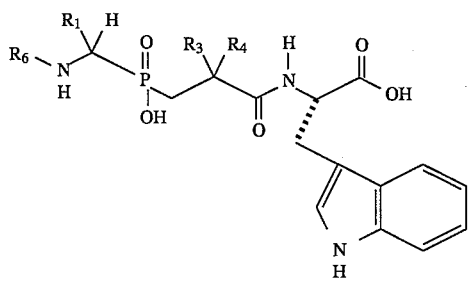

| Isomer | R$_6$ | R$_1$ | R$_3$ | R$_4$ | IC$_{50}$ (nM) |
|---|---|---|---|---|---|
| A | H$_2$N(CH$_2$)$_4$CH(NHMs)C(O)— | 2-naphthylmethyl | H | iso-butyl | 27 |
| B | H$_2$N(CH$_2$)$_4$CH(NHMs)C(O)— | 2-naphthylmethyl | H | iso-butyl | 60 |
| C | H$_2$N(CH$_2$)$_4$CH(NHMs)C(O)— | 2-naphthylmethyl | H | iso-butyl | 68 |
| — | Cbz—NH—CH((CH$_3$)$_2$CHCH$_2$))C(O)— | C$_6$H$_5$—CH$_2$— | H | iso-butyl | 160 |
| — | H$_3$CO—C$_6$H$_4$—C(O)— | C$_6$H$_5$—CH$_2$— | R$_3$ + R$_4$ = —(CH$_2$)$_4$— | | 160 |
| — | Cbz | C$_6$H$_5$—CH$_2$— | R$_3$ + R$_4$ = —(CH$_2$)$_4$— | | 190 |
| — | Cbz | HO—(CH$_2$)$_4$— | H | iso-butyl | 200 |
| — | [structure: CH(iPr)(NHMs)-C(O)-NH-C((CH$_2$)$_4$-NHCbz)-C(O)—] | 2-naphthylmethyl | H | iso-butyl | 230 |
| — | H$_2$N(CH$_2$)$_4$CH(NHCbz)C(O)— | C$_6$H$_5$—CH$_2$— | H | iso-propyl | 250 |
| — | Cbz—NH(CH$_2$)$_4$CH(NHMs)—C(O)— | iso-butyl | R$_3$ + R$_4$ = —(CH$_2$)$_4$— | | 260 |
| — | Cbz | 2-naphthylmethyl | H | iso-butyl | 300 |
| A | Cbz—NH(CH$_2$)$_4$CH(NHMs)—C(O)— | C$_6$H$_5$—CH$_2$— | H | iso-propyl | 390 |
| B | Cbz—NH(CH$_2$)$_4$CH(NHMs)—C(O)— | C$_6$H$_5$—CH$_2$— | H | iso-propyl | 1500 |
| — | Cbz | NH$_2$—(CH$_2$)$_4$— | H | iso-butyl | 400 |
| — | Cbz—NH—CH(iBu)—C(O)— | C$_6$H$_5$—CH$_2$— | H | iso-propyl | 400 |
| — | Cbz | H | R$_3$ + R$_4$ = —(CH$_2$)$_4$— | | 420 |
| — | H$_2$N(CH$_2$)$_4$CH(NHMs)C(O)— | C$_6$H$_5$—CH$_2$— | H | iso-propyl | 500 |
| — | Cbz—NH(CH$_2$)$_4$CH(NHMs)—C(O)— | C$_6$H$_5$—CH$_2$— | H | iso-butyl | 500 |
| — | Cbz | 2-naphthylmethyl | R$_3$ + R$_4$ = —(CH$_2$)$_4$— | | 500 |

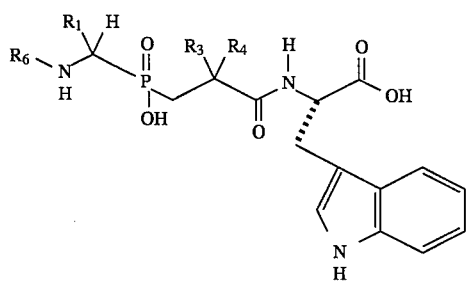

| Isomer | R6 | R1 | R3 | R4 | IC50 (nM) |
|---|---|---|---|---|---|
| — | $H_2N(CH_2)_3CH(NHMs)C(O)$— | $C_6H_5$—$CH_2$— | H | iso-propyl | 550 |
| — | Cbz—$NH(CH_2)_4CH(NHMs)$—C(O)— | 2-naphthylmethyl | H | iso-propyl | 800 |
| — | Cbz | cyclopentylmethyl | H | iso-butyl | 1000 |
| — | Cbz—NH—CH—C(O)—, (CH$_2$)$_4$—NH—Cbz | $C_6H_5$—$CH_2$— | H | iso-propyl | 1100 |
| — | Cbz | $C_6H_5$—$CH_2$— | H | iso-propyl | 1300 |
| — | Cbz—$NH(CH_2)_4CH(NHMs)$—C(O)— | iso-butyl | H | iso-butyl | 1400 |
| — | $H_2N$—CH(iPr)—C(O)— | $C_6H_5$—$CH_2$— | H | iso-propyl | 1600 |

Cbz = carbobenzyloxy;
Ms = methanesulfonyl

We claim:

1. A compound represented by the structural formula

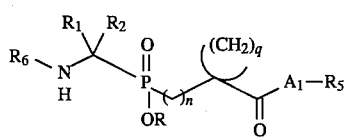

or a pharmaceutically acceptable salt thereof, wherein

R is H, ($C_1$–$C_8$)alkyl or ($C_1$–$C_8$)alkanoyloxymethylene;

$R_1$ and $R_2$, are independently selected from the group consisting of H, ($C_1$–$C_8$)alkyl, ($C_1$–$C_8$)alkenyl, ($C_1$–$C_8$)alkenyl($C_1$–$C_8$)alkyl, aryl, aryl($C_1$–$C_8$)alkyl, hydroxy-($C_1$–$C_8$)alkyl, carboxy($C_1$–$C_8$)alkyl, thio($C_1$–$C_8$)alkyl, ($C_1$–$C_6$)alkoxythio($C_1$–$C_8$)alkyl, amino($C_1$–$C_8$)alkyl, ($C_1$–$C_8$)alkylamino($C_1$–$C_8$)alkyl and cycloalkyl-substituted($C_1$–$C_8$)alkyl; or $R_1$ and $R_2$, together with the carbon to which they are attached, form a cycloalkyl ring of 3 to 8 members;

$R_5$ is —$OR_9$ or —$NHR_9$, wherein $R_9$ is hydrogen or ($C_1$–$C_8$)alkyl;

n is 0 or 1;

q is 2 to 6;

$A_1$ and $R_5$ together are

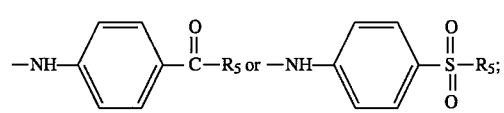

or $A_1$ and $R_5$ together form a radical of an α-aminoacyl derivative, wherein $A_1$ is a divalent α-aminoacyl radical attached to the molecule at the α-amino group, and wherein $R_5$ is attached to the acyl terminus of $A_1$;

$R_6$ is phenylmethoxycarbonyl, arylcarbonyl, or —$A_2$—$R_7$, wherein $A_2$ is a divalent α-aminoacyl radical attached to the molecule at the acyl terminus, and wherein $R_7$ is a substituent on the α-amino atom selected from the group consisting of H, $R_8$OCO—, $R_8SO_2$— and $R_8$NHCO—, wherein $R_8$ is aryl, arylmethyl or ($C_1$–$C_8$)alkyl.

2. A compound of claim 1 wherein n is 1.

3. A compound of claim 1 wherein —$A_1$—$R_5$ is L-tryptophanyl, L-tyrosinyl or L-O-methyl tyrosinyl.

4. A compound of claim 1 wherein $R_1$ and $R_2$ are independently selected from the group consisting of H, aryl($C_1$–$C_8$)alkyl and branched ($C_1$–$C_8$)alkyl.

5. A compound of claim 4 wherein one of $R_1$ and $R_2$ is hydrogen and the other is benzyl, 2-naphthylmethyl, or branched ($C_1$–$C_8$)alkyl.

6. A compound of claim 1 wherein R is hydrogen and $R_5$ is hydroxy.

7. A compound of claim 1 wherein $R_6$ is —$A_2$—$R_7$ or phenyl-methoxycarbonyl.

8. A compound of claim 1 wherein $A_2$ is an α-aminoacyl radical derived from lysine, ε-CBZ lysine, arginine, isoleucine, leucine, valine, phenylalanine, alanine, glycine or tyrosine, and $R_7$ is benzyloxycarbonyl or methansulfonyl.

9. A compound of claim 1 wherein q is 4.

10. A compound of claim 1 wherein n is 1; —$A_1$—$R_5$ is L-tryptophanyl, L-tyrosinyl or L-O-methyl tyrosinyl; $R_1$ and $R_2$ are independently selected from the group consisting of H, aryl($C_1$–$C_8$)alkyl and branched ($C_1$–$C_8$)alkyl; and $R_6$ is —$A_2$—$R_7$ or phenyl-methoxycarbonyl.

11. A compound of claim 10 wherein one of $R_1$ and $R_2$ is hydrogen and the other is benzyl, 2-naphthylmethyl, or branched ($C_1$–$C_8$)alkyl; $A_2$ is an α-aminoacyl radical derived from lysine, ε-CBZ lysine, arginine, isoleucine, leucine, valine, phenylalanine, alanine, glycine or tyrosine; and $R_7$ is benzyloxycarbonyl or methansulfonyl.

12. A compound of claim 11 wherein R is hydrogen, $R_5$ is hydroxy and q is 4.

13. A compound of claim 1 selected from the group consisting of:

N-[[1-[[hydroxy[2-phenyl-1(R)-[[(phenylmethoxy)carbonyl]amino]ethyl]phosphinyl]methyl]cyclopentyl]carbonyl]-L-tryptophan;

N-[[1-[[hydroxy[2-(4-methoxyphenyl)-1(R,S)-[[(phenylmethoxy)carbonyl]amino]ethyl]phosphinyl]methyl]cyclopentyl]carbonyl]-L-tryptophan;

N-[[1-[[hydroxy[2-phenyl-1(R)-[[(phenylmethoxy)carbonyl]amino]ethyl]phosphinyl]methyl]cyclopentyl]carbonyl]-L-tyrosine;

N-[[1-[[hydroxy[2-phenyl-1(R)-[[2(S)-[(methylsulfonyl)amino]-1-oxo-6-[[(phenylmethoxy)carbonyl]amino]hexyl]amino]ethyl]phosphinyl]methyl]cyclopentyl]carbonyl]-L-tryptophan;

N-[[1-[[hydroxy[2-(4-methoxyphenyl)-1(R,S)-[[2(S)-[(methylsulfonyl)amino]-1-oxo-6-[[(phenylmethoxy)carbonyl]amino]hexyl]amino]ethyl]phosphinyl]methyl]cyclopentyl]carbonyl]-L-tryptophan;

N-[[1-[[hydroxy[2-(4-hydroxyphenyl)-1(R,S)-[[2(S)-[(methylsulfonyl)amino]-1 -oxo-6-[[(phenylmethoxy)carbonyl]amino]hexyl]amino]ethyl]phosphinyl]methyl]cyclopentyl]carbonyl]-L-tryptophan;

N-[[1-[[hydroxy[2-phenyl-1(R)-[[2(S)-[(methylsulfonyl)amino]-1-oxo-6-[[(phenylmethoxy)carbonyl]amino]hexyl]amino]ethyl]phosphinyl]methyl]cyclopentyl]carbonyl]-L-tyrosine;

N-[[1-[[hydroxy-[1(R)-[[6-amino-2(S)-[(methylsulfonyl)amino]-1-oxohexyl]amino]-2-phenylethyl]phosphinyl]methyl]cyclopentyl]carbonyl]-L-tryptophan lithium salt;

N-[[1-[[hydroxy-[1(R,S)-[[6-amino-2(S)-[(methylsulfonyl)amino]-1-oxohexyl]amino]-2-(4-methoxyphenyl)ethyl]phosphinyl]methyl]cyclo-pentyl]carbonyl]-L-tryptophan lithium salt;

N-[[1-[[hydroxy-[1(R,S)-[[6-amino-2(S)-[(methylsulfonyl)amino]-1-oxohexyl]amino]-2-(4-hydroxyphenyl)ethyl]phosphinyl]methyl]cyclo-pentyl]carbonyl]-L-tryptophan lithium salt;

N-[[1-[[hydroxy-[1(R)-[[6-amino-2(S)-[(methylsulfonyl)amino]-1-oxohexyl] amino]-2-phenylethyl]phosphinyl]methyl]cyclopentyl]carbonyl]-L-tyrosine lithium salt;

N-[[1-[[hydroxy-[1(R)-[[4-(aminomethyl)benzoyl]amino]-2-phenylethyl]phosphinyl]methyl]cyclopentyl]carbonyl]-L-tryptophan;

N-[[1-[[hydroxy-[1(R)-[[4-nitrobenzoyl]amino]-2-phenylethyl]phosphinyl]methyl]cyclopentyl]carbonyl]-L-tryptophan;

N-[[1-[[hydroxy[2-[4-(4-morpholinecarbonyl)phenyl]-1(R,S)-[[(phenylmethoxy)carbonyl]amino]ethyl]-phosphinyl]methyl]cyclopentyl]carbonyl]-L-tryptophan; and N-[[1-[[hydroxy[2-(4-hydroxyphenyl)-1(R,S)-[[(phenylmethoxy)carbonyl]amino]ethyl]-phosphinyl]methyl]cyclopentyl]carbonyl]-L-tryptophan.

14. A method of inhibiting endothelin converting enzyme comprising administering to a mammal in need of such treatment a compound represented by the structural formula

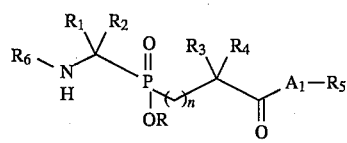

or a pharmaceutically acceptable salt thereof, wherein

R is H, ($C_1$–$C_8$)alkyl or ($C_1$–$C_8$)alkanoyloxymethylene;

$R_1$, $R_2$, $R_3$ and $R_4$ are independently selected from the group consisting of H, ($C_1$–$C_8$)alkyl, ($C_1$–$C_8$)alkenyl, ($C_1$–$C_8$)alkenyl($C_1$–$C_8$)alkyl, aryl, aryl($C_1$–$C_8$)alkyl, hydroxy-($C_1$–$C_8$)alkyl, carboxy($C_1$–$C_8$)alkyl, thio($C_1$–$C_8$)alkyl, ($C_1$–$C_6$)alkoxythio($C_1$–$C_8$)alkyl, amino($C_1$–$C_8$)alkyl, ($C_1$–$C_8$)alkylamino($C_1$–$C_8$)alkyl, and cycloalkyl-substituted($C_1$–$C_8$)alkyl; or $R_1$ and $R_2$, together with the carbon to which they are attached, form a cycloalkyl ring of 3 to 8 members and $R_3$ and $R_4$ are as defined above; or $R_3$ and $R_4$, together with the carbon to which they are attached, form a cycloalkyl ring of 3 to 7 members and $R_1$ and $R_2$ are as defined above; or $R_1$ and $R_2$ together, and $R_3$ and $R_4$ together, each form a cycloalkyl ring as defined above;

$R_5$ is —$OR_9$ or —$NHR_9$, wherein $R_9$ is hydrogen or ($C_1$–$C_8$)alkyl;

n is 0 or 1;

$A_1$ and $R_5$ together are

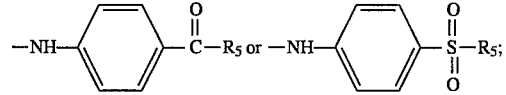

or $A_1$ and $R_5$ together form a radical of an α-aminoacyl derivative, wherein $A_1$ is a divalent α-aminoacyl radical attached to the molecule at the α-amino group, and wherein $R_5$ is attached to the acyl terminus of $A_1$;

$R_6$ is phenylmethoxycarbonyl, arylcarbonyl, or —$A_2$—$R_7$, wherein $A_2$ is a divalent α-aminoacyl radical attached to the molecule at the acyl terminus, and wherein $R_7$ is a substituent on the α-amino atom selected from the group consisting of H, $R_8$OCO—, $R_8SO_2$— and $R_8$NHCO—, wherein $R_8$ is aryl, arylmethyl or ($C_1$–$C_8$)alkyl.

15. A method of claim 14 comprising administering a compound wherein n is 1.

16. A method of claim 14 comprising administering a compound wherein —$A_1$—$R_5$ is L-tryptophanyl, L-tyrosinyl or L-O-methyl tyrosinyl.

17. A method of claim 14 comprising administering a compound wherein $R_1$ and $R_2$ are independently selected from the group consisting of H, aryl($C_1$–$C_8$)alkyl, branched ($C_1$–$C_8$)alkyl and cycloalkyl.

18. A method of claim 17 comprising administering a compound wherein one of $R_1$ and $R_2$ is hydrogen and the other is benzyl, 2-naphthylmethyl, or branched (C$_1$–C$_8$)alkyl.

19. A method of claim 14 comprising administering a compound wherein R$_3$ and R$_4$ are independently selected from the group consisting of hydrogen and (C$_1$–C$_8$)alkyl, or R$_3$ and R$_4$, together with the carbon to which they are attached, form a cycloalkyl ring of 5 or 7 members.

20. A method of claim 19 comprising administering a compound wherein R$_3$ and R$_4$ are independently selected from the group consisting of hydrogen, iso-propyl and iso-butyl.

21. A method of claim 14 comprising administering a compound wherein R is hydrogen and R$_5$ is hydroxy.

22. A method of claim 14 comprising administering a compound wherein R$_6$ is phenylmethoxycarbonyl or —A$_2$—R$_7$.

23. A method of claim 14 comprising administering a compound wherein A$_2$ is an α-aminoacyl radical derived from lysine, ε-CBZ lysine, arginine, isoleucine, leucine, valine, phenylalanine, alanine, glycine or tyrosine, and R$_7$ benzyloxycarbonyl or methansulfonyl.

24. A method of claim 14 comprising administering a compound wherein n is 1; —A$_1$—R$_5$ is L-tryptophanyl, L-tyrosinyl or L-O-methyl tyrosinyl; R$_1$ and R$_2$ are independently selected from the group consisting of H, aryl(C$_1$–C$_8$)alkyl, branched (C$_1$–C$_8$)alkyl and cycloalkyl; and R$_6$ is —A$_2$—R$_7$ or phenyl-methoxycarbonyl.

25. A method of claim 24 comprising administering a compound wherein one of R$_1$ and R$_2$ is hydrogen and the other is benzyl, 2-naphthylmethyl, or branched (C$_1$–C$_8$)alkyl; A$_2$ is an α-aminoacyl radical derived from lysine, ε-CBZ lysine, arginine, isoleucine, leucine, valine, phenylalanine, alanine, glycine or tyrosine; and R$_7$ is benzyloxycarbonyl or methansulfonyl.

26. A method of claim 25 wherein R$_3$ and R$_4$ are independently selected from the group consisting of hydrogen, iso-propyl and iso-butyl.

27. A method of claim 26 wherein R is hydrogen and R$_5$ is hydroxy.

28. A method of claim 14 wherein the compound administered is selected from:

N-[[1-[[hydroxy[2-phenyl-1(R)-[[(phenylmethoxy)carbonyl]amino]ethyl]phosphinyl]methyl]cyclopentyl]carbonyl]-L-tryptophan;

N-[[1-[[hydroxy[2-(4-methoxyphenyl)-1(R,S)-[[(phenylmethoxy)carbonyl]amino]ethyl]phosphinyl]methyl]cyclopentyl]carbonyl]-L-tryptophan;

N-[[1-[[hydroxy[2-phenyl-1(R)-[[(phenylmethoxy)carbonyl]amino]ethyl]phosphinyl]methyl]cyclopentyl]carbonyl]-L-tyrosine;

N-[[1-[[hydroxy[2-phenyl-1(R,S)-[[2(S)-[(methylsulfonyl)amino]-1-oxo-6-[[(phenylmethoxy)carbonyl]amino]hexyl]amino]ethyl]phosphinyl]methyl]cyclopentyl]carbonyl]-L-tryptophan;

N-[[1-[[hydroxy[2-(4-methoxyphenyl)-1(R,S)-[[2(S)-[(methylsulfonyl)amino]-1-oxo-6-[[(phenylmethoxy)carbonyl]amino]hexyl]amino]ethyl]phosphinyl]methyl]cyclopentyl]carbonyl]-L-tryptophan;

N-[[1-[[hydroxy[2-(4-hydroxyphenyl)-1(R)-[[2(S)-[(methylsulfonyl)amino]-1-oxo-6-[[(phenylmethoxy)carbonyl]amino]hexyl]amino]ethyl]phosphinyl]methyl]cyclopentyl]carbonyl]-L-tryptophan;

N-[[1-[[hydroxy[2-phenyl-1(R)-[[2(S)-[(methylsulfonyl)amino]-1-oxo-6-[[(phenylmethoxy)carbonyl]amino]hexyl]amino]ethyl]phosphinyl]methyl]cyclopentyl]carbonyl]-L-tyrosine;

N-[[1-[[hydroxy-[1(R)-[[6-amino-2(S)-[(methylsulfonyl)amino]-1-oxohexyl]amino]-2-phenylethyl]phosphinyl]methyl]cyclopentyl]carbonyl]-L-tryptophan lithium salt;

N-[[1-[[hydroxy-[1(R,S)-[[6-amino-2(S)-[(methylsulfonyl)amino]-1-oxohexyl]amino]-2-(4-methoxyphenyl)ethyl]phosphinyl]methyl]cyclo-pentyl]carbonyl]-L-tryptophan lithium salt;

N-[[1-[[hydroxy-[1(R,S)-[[6-amino-2(S)-[(methylsulfonyl)amino]-1-oxohexyl]amino]-2-(4-hydroxyphenyl)ethyl]phosphinyl]methyl]cyclo-pentyl]carbonyl]-L-tryptophan lithium salt;

N-[[1-[[hydroxy-[1(R)-[[6-amino-2(S)-[(methylsulfonyl)amino]-1-oxohexyl]amino]-2-phenylethyl]phosphinyl]methyl]cyclopentyl]carbonyl]-L-tyrosine lithium salt;

N-[[1-[[hydroxy-[1(R)-[[4-(aminomethyl)benzoyl]amino]-2-phenylethyl]phosphinyl]methyl]cyclopentyl]carbonyl]-L-tryptophan;

N-[[1-[[hydroxy-[1(R)-[[4-nitrobenzoyl]amino]-2-phenylethyl]phosphinyl]methyl]cyclopentyl]carbonyl]-L-tryptophan;

N-[[1-[[hydroxy[2-[4-(4-morpholinecarbonyl)phenyl]-1(R,S)-[[(phenylmethoxy)carbonyl]amino]ethyl]-phosphinyl]methyl]cyclopentyl]carbonyl]-L-tryptophan;

N-[[1-[[hydroxy[2-(4-hydroxyphenyl)-1(R,S)-[[(phenylmethoxy)carbonyl]amino]ethyl]-phosphinyl]methyl]cyclopentyl]carbonyl]-L-tryptophan;

N-[2-[[hydroxy[1-[[2(S)-[(methylsulfonyl)amino]-1-oxo-6-[[phenylmethoxy)carbonyl]amino]hexyl]amino]-2-(2-naphthalenyl)ethyl]phosphinyl]methyl]-4-methyl-1-oxopentyl]-L-tryptophan disodium salt; and N-[2-[[hydroxy[3-methyl-1-[[2-[(methylsulfonyl)amino]-1-oxo-6-[[ phenylmethoxy)-carbonyl]amino]hexyl]amino]butyl]phosphinyl]methyl]-4-methyl-1-oxopentyl]-L-tryptophan disodium salt.

29. A pharmaceutical composition comprising an amount of a compound of claim 1 effective to inhibit endothelin converting enzyme in a mammal in need of such treatment in a pharmaceutically acceptable carrier.

\* \* \* \* \*